[19] United States Patent
Schreck et al.

(10) Patent No.: US 9,687,263 B2
(45) Date of Patent: Jun. 27, 2017

(54) DEVICES AND METHODS FOR INSERTING A SINUS DILATOR

(71) Applicant: SinuSys Corporation, Palo Alto, CA (US)

(72) Inventors: Thomas A. Schreck, Portola Valley, CA (US); Jerome E. Hester, Menlo Park, CA (US); David E. Edgren, Los Altos, CA (US); William Jason Fox, San Carlos, CA (US); Curtis Leslie Rieser, San Jose, CA (US)

(73) Assignee: SinuSys Corporation, Palo Alto, CA (US)

( * ) Notice: Subject to any disclaimer, the term of this patent is extended or adjusted under 35 U.S.C. 154(b) by 419 days.

(21) Appl. No.: 14/290,655

(22) Filed: May 29, 2014

(65) Prior Publication Data

US 2014/0358177 A1 Dec. 4, 2014

Related U.S. Application Data

(60) Provisional application No. 61/829,023, filed on May 30, 2013, provisional application No. 61/865,931, filed on Aug. 14, 2013.

(51) Int. Cl.
*A61B 17/24* (2006.01)
*A61B 17/34* (2006.01)
(Continued)

(52) U.S. Cl.
CPC .......... *A61B 17/24* (2013.01); *A61B 17/3468* (2013.01); *A61B 90/361* (2016.02);
(Continued)

(58) Field of Classification Search
CPC ............ A61B 17/3468; A61B 17/3462; A61B 2017/1205; A61B 2017/00469;
(Continued)

(56) References Cited

U.S. PATENT DOCUMENTS 3,625,351 A 12/1971 Eisenberg
3,732,865 A 5/1973 Higuchi et al.
(Continued)

FOREIGN PATENT DOCUMENTS

EP 0923912 6/1999
JP AH4-215768 2/1994
(Continued)

OTHER PUBLICATIONS

Sehgal et al., (1975) "Rapamycin (AY-22,989), a new antifungal antibiotic. 11. Fermentation, isolation and characterization." J. Antibiot 28(10): 727-732. Abstract Only.
(Continued)

*Primary Examiner* — Katrina Stransky
(74) *Attorney, Agent, or Firm* — Rudy J. Ng; Carol Francis; Bozicevic, Field & Francis LLP

(57) ABSTRACT

Devices that are adapted to insert a sinus dilator into a stenotic opening of a paranasal sinus of a subject using minimally invasive dilator insertion procedures are provided. The devices and methods can be used to treat sinusitis and other nasal and/or sinus disorders.

26 Claims, 9 Drawing Sheets

(51) Int. Cl.
*A61B 17/00* (2006.01)
*A61B 90/00* (2016.01)

(52) U.S. Cl.
CPC ............... *A61B 2017/00331* (2013.01); *A61B 2017/00469* (2013.01); *A61B 2017/00867* (2013.01); *A61B 2017/00898* (2013.01); *A61M 2205/0266* (2013.01); *A61M 2210/0681* (2013.01)

(58) Field of Classification Search
CPC  A61B 2017/00867; A61B 2017/00898; A61B 17/24; A61B 17/12104; A61B 2017/00331; A61B 1/233; A61B 17/1688; A61M 2205/0266; A61M 2210/0681
USPC ......................................................... 606/199
See application file for complete search history.

(56) References Cited

U.S. PATENT DOCUMENTS

| | | | |
|---|---|---|---|
| 3,760,805 A | 9/1973 | Higuchi | |
| 3,760,984 A | 9/1973 | Theeuwes | |
| 3,786,813 A | 1/1974 | Michaels | |
| 3,845,770 A | 11/1974 | Theeuwes et al. | |
| 4,014,334 A | 3/1977 | Theeuwes et al. | |
| 4,142,526 A | 3/1979 | Zaffaroni et al. | |
| 4,203,440 A | 5/1980 | Theeuwes | |
| 4,203,441 A | 5/1980 | Theeuwes | |
| 4,449,983 A | 5/1984 | Cortese | |
| 4,455,143 A | 6/1984 | Theeuwes | |
| 4,467,806 A | 8/1984 | Bhiwandiwala et al. | |
| 4,480,642 A | 11/1984 | Stoy et al. | |
| 4,663,148 A | 5/1987 | Eckenhoff et al. | |
| 5,160,743 A | 11/1992 | Edgren et al. | |
| 5,234,456 A | 8/1993 | Silvestrini | |
| 5,246,455 A | 9/1993 | Shikani | |
| 5,258,042 A | 11/1993 | Mehta | |
| 5,336,163 A | 8/1994 | DeMane et al. | |
| 5,413,572 A | 5/1995 | Wong et al. | |
| 5,423,745 A | 6/1995 | Todd et al. | |
| 5,464,450 A | 11/1995 | Buscemi et al. | |
| 5,496,368 A | 3/1996 | Wiese | |
| 5,498,255 A | 3/1996 | Wong | |
| 5,499,994 A | 3/1996 | Tihon et al. | |
| 5,500,013 A | 3/1996 | Buscemi et al. | |
| 5,547,378 A | 8/1996 | Linkow | |
| 5,674,241 A | 10/1997 | Bley et al. | |
| 5,693,065 A | 12/1997 | Rains, III | |
| 5,713,855 A | 2/1998 | Shippert | |
| 5,716,329 A | 2/1998 | Dieter | |
| 5,728,396 A | 3/1998 | Peery et al. | |
| 6,056,720 A | 5/2000 | Morse | |
| 6,123,697 A | 9/2000 | Shippert | |
| 6,224,907 B1 | 5/2001 | Davar et al. | |
| 6,270,787 B1 | 8/2001 | Ayer | |
| 6,336,496 B1 | 1/2002 | Asai et al. | |
| 6,387,124 B1 | 5/2002 | Buscemi et al. | |
| 6,455,065 B1 | 9/2002 | Hymes | |
| 6,648,873 B2 | 11/2003 | Arenberg et al. | |
| 6,753,011 B2 | 6/2004 | Faour | |
| 6,976,983 B2 | 12/2005 | Russell | |
| 7,014,636 B2 | 3/2006 | Gilbert | |
| 7,074,423 B2 | 7/2006 | Fereira et al. | |
| 7,108,684 B2 | 9/2006 | Farnan | |
| 7,108,762 B2 | 9/2006 | Russell | |
| 7,211,076 B2 | 5/2007 | Russell | |
| 7,235,068 B2 | 6/2007 | Theeuwes et al. | |
| 7,235,099 B1 | 6/2007 | Duncavage et al. | |
| 7,241,457 B2 | 7/2007 | Chen et al. | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,544,192 B2 | 6/2009 | Eaton et al. | |
| 7,591,830 B2 | 9/2009 | Rutter | |
| 7,645,272 B2 | 1/2010 | Chang et al. | |
| 7,654,997 B2 | 2/2010 | Makower et al. | |
| 7,655,257 B2 | 2/2010 | Perry et al. | |
| 7,678,099 B2 | 3/2010 | Ressemann et al. | |
| 7,678,103 B2 | 3/2010 | Russell | |
| 7,740,642 B2 | 6/2010 | Becker | |
| 7,740,643 B2 | 6/2010 | Maryanka | |
| 2002/0004060 A1 | 1/2002 | Heublein et al. | |
| 2002/0088723 A1 | 7/2002 | Lowry et al. | |
| 2002/0120276 A1 | 8/2002 | Greene et al. | |
| 2003/0171773 A1 | 9/2003 | Carrison | |
| 2004/0064150 A1 | 4/2004 | Becker | |
| 2004/0073299 A1 | 4/2004 | Hudson et al. | |
| 2004/0098095 A1 | 5/2004 | Burnside et al. | |
| 2004/0098108 A1 | 5/2004 | Harder et al. | |
| 2004/0116958 A1 | 6/2004 | Gopferich et al. | |
| 2004/0127871 A1 | 7/2004 | Odorzynski et al. | |
| 2004/0243214 A1 | 12/2004 | Farrell | |
| 2004/0267241 A1 | 12/2004 | Russell | |
| 2005/0054999 A1 | 3/2005 | Morman et al. | |
| 2005/0149173 A1 | 7/2005 | Hunter et al. | |
| 2005/0165379 A1 | 7/2005 | Mawad | |
| 2005/0240147 A1 | 10/2005 | Makower et al. | |
| 2005/0268573 A1 | 12/2005 | Yan | |
| 2005/0278012 A1 | 12/2005 | Vonderwalde | |
| 2006/0047247 A1 | 3/2006 | Anders | |
| 2006/0063973 A1 | 3/2006 | Makower et al. | |
| 2006/0106361 A1 | 5/2006 | Muni et al. | |
| 2006/0276831 A1 | 12/2006 | Porter et al. | |
| 2007/0005094 A1 | 1/2007 | Eaton et al. | |
| 2007/0073269 A1 | 3/2007 | Becker | |
| 2007/0084144 A1 | 4/2007 | Labrecque et al. | |
| 2007/0106233 A1 | 5/2007 | Huang | |
| 2007/0129751 A1 | 6/2007 | Muni et al. | |
| 2007/0156251 A1 | 7/2007 | Karmon | |
| 2007/0160647 A1 | 7/2007 | Pritchard et al. | |
| 2007/0233036 A1 | 10/2007 | Mandpe | |
| 2007/0244562 A1 | 10/2007 | Conner et al. | |
| 2007/0250105 A1 | 10/2007 | Ressemann et al. | |
| 2007/0269385 A1 | 11/2007 | Yun et al. | |
| 2007/0299392 A1 | 12/2007 | Beyar et al. | |
| 2008/0044553 A1 | 2/2008 | Freeman et al. | |
| 2008/0082045 A1 | 4/2008 | Goldfarb et al. | |
| 2008/0097468 A1 | 4/2008 | Adams et al. | |
| 2008/0125805 A1 | 5/2008 | Mische | |
| 2008/0243140 A1 | 10/2008 | Gopferich et al. | |
| 2008/0264102 A1 | 10/2008 | Berra | |
| 2008/0292255 A1 | 11/2008 | Stevens et al. | |
| 2009/0036968 A1 | 2/2009 | Hepworth et al. | |
| 2009/0098184 A1 | 4/2009 | Govil et al. | |
| 2009/0125046 A1 | 5/2009 | Becker | |
| 2009/0187098 A1* | 7/2009 | Makower | A61B 1/0661 600/424 |
| 2009/0220571 A1 | 9/2009 | Eaton et al. | |
| 2009/0248141 A1 | 10/2009 | Shandas et al. | |
| 2009/0264976 A1 | 10/2009 | Nagasrinivasa | |
| 2009/0312745 A1 | 12/2009 | Goldfarb et al. | |
| 2009/0314676 A1 | 12/2009 | Peck et al. | |
| 2010/0030113 A1* | 2/2010 | Morriss | A61B 1/233 600/585 |
| 2010/0076269 A1 | 3/2010 | Makower et al. | |
| 2010/0099946 A1 | 4/2010 | Jenkins et al. | |
| 2010/0100116 A1 | 4/2010 | Brister et al. | |
| 2010/0106255 A1 | 4/2010 | Dubin | |
| 2010/0155282 A1 | 6/2010 | Govil et al. | |
| 2010/0198191 A1 | 8/2010 | Clifford et al. | |
| 2010/0298862 A1* | 11/2010 | Chang | A61B 17/24 606/199 |
| 2010/0305603 A1 | 12/2010 | Nielsen et al. | |
| 2010/0312101 A1 | 12/2010 | Drontle et al. | |
| 2010/0312338 A1 | 12/2010 | Gonzales et al. | |
| 2011/0004057 A1 | 1/2011 | Goldfarb et al. | |
| 2011/0021975 A1 | 1/2011 | Covello | |
| 2011/0125091 A1 | 5/2011 | Abbate | |
| 2012/0053404 A1 | 3/2012 | Schreck et al. | |
| 2012/0053567 A1 | 3/2012 | Schreck et al. | |

(56) References Cited

U.S. PATENT DOCUMENTS

| | | | |
|---|---|---|---|
| 2012/0071727 A1 | 3/2012 | Hanson et al. | |
| 2012/0116350 A1 | 5/2012 | Strauss et al. | |
| 2012/0261290 A1 | 10/2012 | Limjaroen et al. | |
| 2013/0072958 A1* | 3/2013 | Ressemann | A61B 17/24 606/199 |
| 2013/0138132 A1 | 5/2013 | Phee et al. | |
| 2013/0231693 A1 | 9/2013 | Edgren et al. | |
| 2013/0253564 A1 | 9/2013 | Edgren et al. | |
| 2013/0253567 A1 | 9/2013 | Edgren et al. | |
| 2013/0261550 A1 | 10/2013 | Edgren et al. | |
| 2013/0267987 A1 | 10/2013 | Edgren et al. | |
| 2014/0031852 A1 | 1/2014 | Edgren et al. | |
| 2015/0065810 A1 | 3/2015 | Edgren et al. | |
| 2016/0121088 A1 | 5/2016 | Fox et al. | |

FOREIGN PATENT DOCUMENTS

| | | |
|---|---|---|
| JP | AH5-76602 | 8/1994 |
| WO | WO 9503848 | 2/1995 |
| WO | WO 9829148 | 7/1998 |
| WO | 9962430 | 12/1999 |
| WO | WO 0247558 | 6/2002 |
| WO | WO 2006034008 | 3/2006 |
| WO | 2006020180 | 6/2006 |
| WO | 2007054108 | 5/2007 |
| WO | WO 2008008389 | 1/2008 |
| WO | WO 2009018248 | 2/2009 |
| WO | WO 2010033629 | 3/2010 |
| WO | 2005117755 | 12/2012 |

OTHER PUBLICATIONS

Mazzoli et al. (2004) "Use of self-expanding, hydrophilic osmotic expanders (hydrogel) in the reconstruction of congenital clinical anophthalmos," Database Medline XP002746291, Accession No. NLM15625905, 2 pgs.

Ronert et al. (2004) "The Beginning of a New Era in Tissue Expansion: Self-Filling Osmotic Tissue Expander—Four-Year Clinical Experience," Plastic and Reconstructive Surgery 114(5)1025-1031.

Merriam-Webster definition of "conduit" as accessed Oct. 6, 2016: http://www.merriam-webster.com/dictionary /conduit 1 page.

Merriam-Webster definition of "channel" as accessed Oct. 6, 2016; http://www.merriam-webster.com/dictionary/channel 1 page.

* cited by examiner

DEVICES AND METHODS FOR INSERTING A SINUS DILATOR

CROSS-REFERENCE TO RELATED APPLICATIONS

Pursuant to 35 U.S.C. §119(e), this application claims priority to the filing date of U.S. Provisional Application No. 61/829,023, filed May 30, 2013, and U.S. Provisional Application No. 61/865,931, filed Aug. 14, 2013, the disclosures of each of which are incorporated herein by reference.

INTRODUCTION

The bones in the skull and face contain a series of air-filled cavities known as paranasal sinuses that are connected by passageways. The paranasal sinuses include frontal sinuses, sphenoid sinuses and maxillary sinuses. The paranasal sinuses are lined with mucus-producing epithelial tissue and are in communication with the nasal cavity. Normally, mucus produced by the epithelial tissue slowly drains out of each sinus through an opening known as an ostium. If the epithelial tissue of one of these passageways becomes inflamed for any reason, the cavities which drain through that passageway can become blocked. This blockage can be periodic (resulting in episodes of pain) or chronic. This interference with drainage of mucus (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months) results in 18 million to 22 million physician office visits per year in the United States. Patients who suffer from sinusitis typically experience at least some of the following symptoms: headaches or facial pain, nasal congestion or post-nasal drainage, difficulty breathing through one or both nostrils, bad breath and/or pain in the upper teeth. Thus, one of the ways to treat sinusitis is by restoring the lost mucus flow.

SUMMARY

Devices that are adapted to insert a sinus dilator into a stenotic opening of a paranasal sinus of a subject using minimally invasive dilator insertion procedures are provided. The devices and methods can be used to treat sinusitis and other nasal and/or sinus disorders.

Embodiments of the present disclosure include a device for inserting a sinus dilator into a stenotic opening of a paranasal sinus of a subject. The insertion device includes a handheld member having a handle and an actuator, a hollow elongated member having a proximal end coupled to the handheld member and a distal end having an opening to an interior cavity of the hollow elongated member, an interior elongated member operatively connected to the actuator and extending within the interior cavity of the hollow elongated member, and a tube engaged to the distal end of the hollow elongated member, where the tube includes a material configured to transition from a first configuration to a second configuration, the first configuration such that the tube is aligned with a longitudinal axis of the hollow elongated member and the second configuration such that the tube is bent relative to the longitudinal axis of the hollow elongated member.

In some embodiments, the material includes a shape-memory material. In some embodiments, the shape-memory material includes a shape-memory alloy. In some embodiments, the shape-memory alloy includes nickel and titanium. In some embodiments, the shape-memory material includes a shape-memory polymer. In some embodiments, the shape-memory polymer includes polyurethane, polyethylene terephthalate (PET), polyethyleneoxide (PEO), polystyrene, polybutadiene, polyoxazoline, polytetrahydrofuran, polynorbornene, polyether ether ketone (PEEK), or combinations thereof.

In some embodiments, a portion of the tube includes a hydrophilic material. In some embodiments, the tube includes an inner tube with the hydrophilic material disposed on a portion of an outer surface of the inner tube.

In some embodiments, the second configuration is such that the tube has a bend angle of 60° to 120° relative to the longitudinal axis of the hollow elongated member. In some embodiments, the bend angle is 110°. In some embodiments, the bend angle is 70°.

In some embodiments, the interior elongated member is relatively displaceable with respect to the hollow elongated member such that upon actuation of the actuator, the interior elongated member is displaced within the hollow elongated member.

In some embodiments, the tube is slidably engaged to an exterior surface of the hollow elongated member.

In some embodiments, the tube is slidably engaged to an interior surface of the hollow elongated member.

In some embodiments, the insertion device includes a sinus dilator operatively coupled to the insertion device. In some embodiments, the sinus dilator is coupled to a distal end of the tube. In some embodiments, the sinus dilator is positioned within the hollow elongated member.

In some embodiments, the tube is radially expandable.

Embodiments of the present disclosure include a method of inserting a sinus dilator in a stenotic opening of a paranasal sinus in a subject. The method includes placing the distal end of the hollow elongated member of the insertion device according to the embodiments disclosed herein into a nasal cavity of the subject, inserting a sinus dilator in the stenotic opening, and removing the insertion device from the nasal cavity of the subject.

In some embodiments, the method includes extending the tube from the distal end of the hollow elongated member.

In some embodiments, inserting the sinus dilator includes relatively displacing the interior elongated member with respect to the hollow elongated member and the tube while the hollow elongated member remains in a relatively fixed position to the handheld member.

In some embodiments, the inserting occurs while the tube is in the second configuration. In some embodiments, the sinus dilator is coupled to a distal end of the tube, and inserting the sinus dilator includes distally displacing the interior elongated member within the hollow elongated member and the tube. In some embodiments, the sinus dilator is positioned within the hollow elongated member and operatively coupled to a distal end of the interior elongated member, and inserting the sinus dilator includes distally displacing the interior elongated member and the sinus dilator through the hollow elongated member and the tube.

In some embodiments, the stenotic opening is a stenotic opening of a maxillary sinus of the subject.

Embodiments of the present disclosure include a kit that includes an insertion device according to the embodiments disclosed herein, and a sinus dilator.

Figure 1:
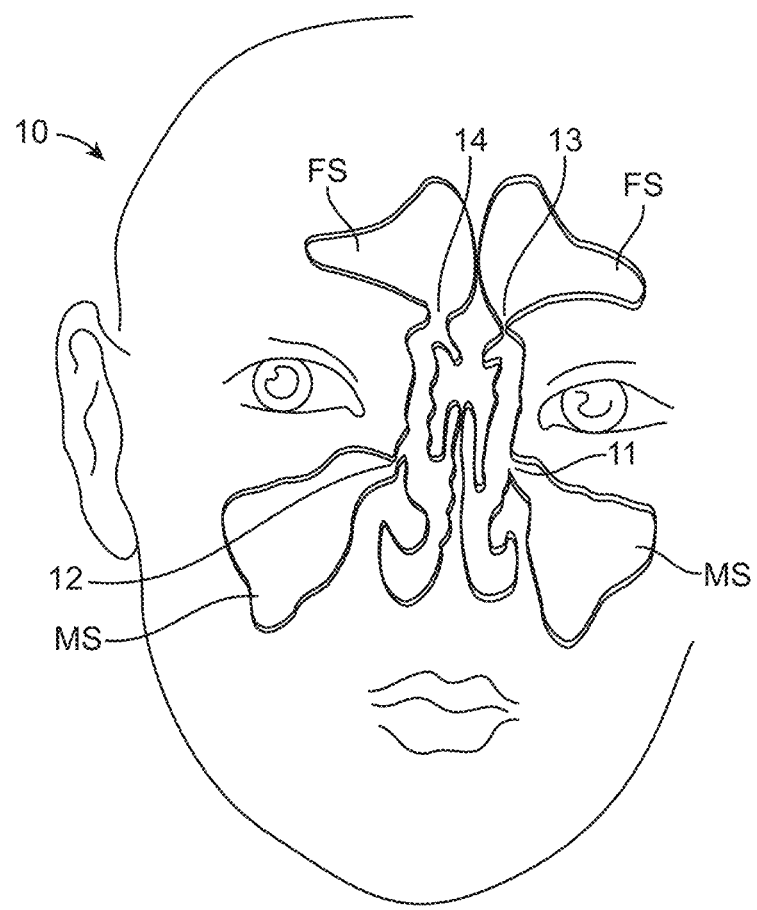
FIG. 1 shows a partial cutaway view of a human head showing the positions of the frontal sinuses (FS) and the maxillary sinuses (MS).

Before embodiments of the present disclosure are described in greater detail, it is to be understood that these embodiments are not limited to the particular aspects described, and as such may, of course, vary. It is also to be understood that the terminology used herein is for the purpose of describing particular embodiments only, and is not intended to be limiting, since the scope of the embodiments is embodied by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within the embodiments, subject to any specifically excluded limit in the stated range. Where the stated range includes one or both of the limits, ranges excluding either or both of those included limits are also included in the embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present embodiments, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, it will be readily apparent to one of ordinary skill in the art in light of the teachings herein that certain changes and modifications may be made thereto without departing from the spirit and scope of the appended claims. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. To the extent such publications may set out definitions of a term that conflict with the explicit or implicit definition of the present disclosure, the definition of the present disclosure controls. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

DETAILED DESCRIPTION

Devices that are adapted to insert a sinus dilator into a stenotic opening of a paranasal sinus of a subject using minimally invasive dilator insertion procedures are provided. The devices and methods can be used to treat sinusitis and other nasal and/or sinus disorders.

Devices and Methods for Inserting a Sinus Dilator

Aspects of the present disclosure include an insertion device adapted to insert a sinus dilator into a stenotic opening of a paranasal sinus in a subject patient using minimally invasive insertion procedures. The insertion device and methods can be used to treat sinusitis and other nasal and/or sinus disorders.

The insertion device includes a handheld member coupled to a hollow elongated member. By "hollow" is meant that the hollow elongated member includes a central passageway that extends through the length of the hollow elongated member. For example, the hollow elongated member may be a tube or a cannula. In certain embodiments, the proximal end of the hollow elongated member may be coupled to a handheld member and the distal end of the hollow elongated member is dimensioned to pass through a nostril and into a nasal cavity of a subject. A sinus dilator may be removably coupled to the insertion device. The sinus dilator is then positioned in a stenotic sinus opening, which may be partially or completely occluded.

In certain embodiments, the insertion device also includes an interior elongated member positioned within the hollow elongated member and extending at least a portion of the length of the hollow elongated member. The interior elongated member has a proximal end coupled to an actuator on the handheld member and dimensioned to fit within the hollow elongated member. The distal end of the interior elongated member may include an interface that contacts and deploys the sinus dilator. In some cases, the sinus dilator may be removably coupled to the insertion device (e.g., slid on, snapped on, clamped on, etc.) and then the distal end of the insertion device may be inserted within the nasal cavity to position the sinus dilator in the stenotic opening. In certain embodiments, the insertion device and sinus dilator are configured to be removably coupled, thus the sinus dilator may be decoupled from the insertion device and left in the stenotic opening.

The insertion device may include various coupling mechanisms to retain the sinus dilator coupled to the insertion device. In some instances, the insertion device includes an interface that is sized and shaped to fit within a sinus dilator, e.g., within a central passageway of the sinus dilator, or a passageway, recess, slot, etc. within the sinus dilator. In certain embodiments, the interface includes one or more slots sized and shaped to accommodate a portion of the sinus dilator. For example, the interface may include a slot configured to accommodate an anchor (e.g., a proximal anchor) of the sinus dilator. The interface may provide sufficient retention to maintain the sinus dilator coupled while permitting some light axial and off-axis loads or bending moments. In some instances, the sinus dilator is sufficiently rigidly affixed to the interface to enable a user (e.g., physician) to push the sinus dilator through a stenotic opening even when the opening is completely shut. In some embodiments, the interface is located at the distal end of the interior elongated member. In other embodiments, the interface is located at a distal end of a tube engaged to the distal end of the hollow elongated member, as described in more detail below.

As summarized above, the insertion device also includes a handheld member. As the handheld member is held by the user, it is configured to have a shape and size that is amenable to gripping by the user's hand. In certain embodiments, the insertion device includes an actuator. The actuator may be operatively connected to the interior elongated member of the insertion device. For example, the actuator may be coupled to at or near the proximal end of the interior elongated member. The actuator may be shaped and sized to be activated by a user (e.g., physician) with the actuator accessible to the user's hand while gripping the handheld member, e.g., actuated by the user's thumb, actuated by a user's index finger, etc. The actuator may, for example, be configured to couple to the interior elongated member, such that movement of the actuator is translated to a corresponding movement of the distal end of the interior elongated member, and if present, to a sinus dilator that may be in contact with the distal end of the interior elongated member.

In certain embodiments, the actuator is slidably engaged to the handheld member. For instance, the actuator may be slidably engaged to the handheld member such that the actuator may be translated in a distal and/or a proximal direction relative to the handheld member. As described above, the actuator may be operatively connected to a proximal end of the interior elongated member, such that movement of the actuator results in a corresponding movement of the interior elongated member. For example, translation of the actuator in a distal direction relative to the handheld member may result in a corresponding distal translation of the interior elongated member within the hollow elongated member as the hollow elongated member remains in a substantially fixed position relative to the handheld member. Similarly, translation of the actuator in a proximal direction relative to the handheld member may result in a corresponding proximal translation of the interior elongated member within the hollow elongated member. As described above, a sinus dilator may be coupled to an interface at the distal end of the interior elongated member. As such, actuation of the interior elongated member by the actuator may result in a corresponding movement of the sinus dilator relative to the handheld member and/or the hollow elongated member as described above. In some cases, an electrical circuit can be created to actuate the mechanical translation of the interior elongated member, such as, for example by electrical actuation of a solenoid element.

Upon activation of the actuator, the interface may be decoupled from the sinus dilator. For example, the interior elongated member may be relatively displaced with respect to the hollow elongated member. In some embodiments, the relative displacing of the interior elongated member with respect to the hollow elongated member includes proximally displacing the interface within the hollow elongated member while the hollow elongated member remains in a substantially fixed position relative to the handheld member. For example, the actuation of the actuator may cause the interface to displace such that at least a portion of the interface that is outside of the distal end of the hollow elongated member is displaced proximally within the hollow elongated member. In some instances, the distal tip of the hollow elongated member may provide a stop against which the sinus dilator is pulled against as all or part of the interface is displaced proximally within the hollow elongated member. In some cases, actuation of the actuator in the embodiments described above decouples the sinus dilator from the insertion device as the interface is displaced proximally with respect to the hollow elongated member.

In other embodiments, the interface may be located at the distal end of the hollow elongated member or at the distal end of a tube engaged to the distal end of the hollow elongated member, such that the sinus dilator is coupled to the distal end of the hollow elongated member or the distal end of the tube. In these embodiments, the relative displacing of the interior elongated member with respect to the hollow elongated member includes distally displacing the interior elongated member within the hollow elongated member while the hollow elongated member remains in a substantially fixed position relative to the handheld member. For example, the actuation of the actuator may cause the interior elongated member to displace such that at least a portion of the interior elongated member that is inside of the distal end of the hollow elongated member is displaced distally within the hollow elongated member. In some instances, the distal tip of the interior elongated member may push against the sinus dilator as the interior elongated member is displaced distally within the hollow elongated member. In some cases, actuation of the actuator in the embodiments described above decouples the sinus dilator from the interface of the insertion device as the distal tip of the interior elongated member is displaced distally with respect to the hollow elongated member.

In certain embodiments, the actuator is configured to be accessible to the user from any gripping position as the user holds the insertion device during use. For example, the insertion device may be rotated about its longitudinal axis to any angle relative to the user's hand, and the actuator may be maintained in a convenient position for actuation by the user. In some cases, to facilitate actuation of the actuator from any hand position as described above, the insertion device includes an actuator that extends around the exterior surface of the handle of the insertion device. For instance, the actuator may extend around 25% or more of the exterior surface of the handle, such as 50% or more, or 75% or more. In some cases, the actuator extends substantially entirely around the exterior surface of the handle. For example, the actuator may extend completely around the circumference of the exterior surface of the handle. As such, the insertion device may be rotated about its longitudinal axis to any angle relative to the user's hand, and the actuator will be in a convenient position for actuation by the user.

In certain embodiments, the insertion device includes a tube engaged to the distal end of the hollow elongated member. In some cases, the tube includes a material configured to transition from a first configuration to a second configuration. For instance, the first configuration may be such that the tube is substantially aligned with a longitudinal axis of the hollow elongated member. In some cases, the first configuration is such that the longitudinal axis of the tube is substantially parallel to the longitudinal axis of the hollow elongated member.

In some instances, in the first configuration the tube and the hollow elongated member are configured as concentric tubes. In certain cases, the tube is engaged to an exterior surface of the hollow elongated member. In other cases, the tube is engaged to an interior surface of the hollow elongated member. In certain embodiments, the tube is slidably engaged to the hollow elongated member. For example, the tube may be slidably engaged to an exterior surface of the hollow elongated member. In other instances, the tube is slidably engaged to an interior surface of the hollow elongated member. In embodiments where the tube is slidably engaged to the hollow elongated member, the tube may be displaced relative to the hollow elongated member. For instance, the tube may be distally displaced relative to the hollow elongated member such that the distal end of the tube extends away from the distal end of the hollow elongated member. Extending the distal end of the tube may facilitate positioning and insertion of the sinus dilator in the stenotic opening of the subject. The tube may also be displaced proximally with respect to the hollow elongated member. For example, after placement of the sinus dilator in the stenotic opening, the tube may be displaced proximally with respect to the hollow elongated member to facilitate removal of the insertion device from the nasal cavity of the subject.

In certain embodiments, the tube has a second configuration such that the tube is bent relative to the longitudinal axis of the hollow elongated member. In the second configuration, the distal end of the tube may be at an angle with respect to the longitudinal axis of the hollow elongated member. In certain embodiments, the tube is configured to transition from the first configuration to the second configuration. In some instances, the tube is configured to assume a predetermined bend configuration (e.g., the second configuration). In some cases, the tube is configured to transition from the first configuration to the second configuration without external input from the user. For instance, the tube may transition from the first configuration to the second configuration without the application of an external bending force on the tube.

In certain embodiments, the tube is an elongated tube having a distal end, a proximal end, and an axial lumen extending from the distal end to the proximal end. In some cases, the tube includes a tubular braid. The tube may be composed of a mesh of round filaments, flat or ribbon filaments, square filaments, or the like. In some embodiments, the filament width or diameter may be from about 0.01 mm to 5 mm, such as from 0.01 to 4 mm, or from 0.01 to 3 mm, or from 0.01 to 2 mm, or from 0.01 to 1 mm, or from 0.05 to 1 mm or from 0.1 to 1 mm or from 0.5 to 1 mm.

The tube may be uncovered or may be laminated or covered with a coating or layer of elastic or plastically deformable material, such as silicone rubber, latex, polyethylene, tetrafluoroethylene, fluorinated ethylene-propylene, or the like. For example, the tube may include a sheath covering at least a portion of the tube. In some instances, the sheath protects the tubular braid of the tube during use.

In certain embodiments, the tube includes a shape-memory material. As used herein, a "shape-memory material" includes materials that have a predetermined geometry (e.g., shape) to which the structure made from the material returns after being elastically deformed. For instance, the shape-memory material can include, but is not limited to, materials that return to its predetermined geometry due to thermal energy (e.g., temperature), such as Nitinol, and/or the influence of a magnetic field. For example, in some instances, the shape-memory material may have a first shape and a second shape, e.g., the first configuration and the second configuration described above. In some cases, the shape-memory material may be configured to conform to the second shape after being deformed into the first shape. For example, the shape-memory material may be deformed into the first configuration described above, where the tube is substantially aligned with the longitudinal axis of the hollow elongated member. In some instances, the shape-memory material is held in the first configuration by the hollow elongated member. For instance, the shape-memory material may be a concentric tube engaged to an exterior or an interior surface of the hollow elongated member as described above. In some instances, the hollow elongated member has a stiffness greater than the shape-memory material such that the shape-memory material is held in the first configuration. As described above, in some instances, the tube may be extended away from the distal end of the hollow elongated member. Extension of the tube from the hollow elongated member may allow the shape-memory material to conform to the second (e.g., bent) configuration.

In certain embodiments, the shape-memory material includes a material such as, but not limited to a shape-memory alloy or a shape-memory polymer. In some cases, the shape-memory alloy includes, but is not limited to, a nickel-titanium alloy (e.g., Nitinol), a silver-cadmium alloy, a gold-cadmium alloy, a copper-aluminum-nickel alloy, a copper-tin alloy, a copper-zinc alloy, a copper-zinc-silicon alloy, a copper-zinc-aluminum alloy, a copper-zinc-tin alloy, an iron-platinum alloy, a manganese-copper alloy, an iron-manganese-silicon alloy, a platinum alloy, a cobalt-nickel-aluminum alloy, a cobalt-nickel-gallium alloy, a nickel-iron-gallium alloy, a titanium-palladium alloy, a nickel-titanium alloy, and nickel-titanium-niobium alloy, a nickel-manganese-gallium alloy, combinations thereof, and the like. In certain instance, the shape-memory alloy includes a nickel-titanium alloy (e.g., Nitinol), such as a nickel-titanium alloy that includes 50-60% nickel and 40-50% titanium, such as 55% nickel and 45% titanium. In certain embodiments, the shape-memory material includes a shape-memory polymer, such as, but not limited to, polyurethane, polyethylene terephthalate (PET), polyethyleneoxide (PEO), polystyrene, polybutadiene, polyoxazoline, polytetrahydrofuran, polynorbornene, polyether ether ketone (PEEK), or combinations thereof, and the like.

In certain embodiments, the tube includes a water swellable material, such as a hydrophilic material. In these embodiments, when placed in an aqueous environment (e.g., where water may be absorbed form the surrounding environment such as a patient's tissues), the water swellable material (e.g., the hydrophilic material) may absorb water in situ and increase in size (e.g., swell). In some cases, the water swellable material is configured to swell in one or more of an axial direction, a longitudinal direction, or in both the axial and longitudinal directions. In certain instances, the water swellable material is localized on a portion of the tube (e.g., on one side of the tube). In these instances, the net effect of this localized swelling is to place the tube into a curved configuration. In some cases, the resulting curved configuration facilitates placement of the insertion device (e.g., the distal tip of the tube) into the opening of the target ostia.

In some instances, the water swellable material (e.g., the hydrophilic material) is disposed on a portion of the tube. For instance, the tube may include an inner tube covered or coated on a portion of an outer surface of the inner tube with the water swellable material, such as on one side of the outer surface of the inner tube. The inner tube may be coated with the water swellable material on a portion of the outer surface of the tube, on a portion of the inner surface of the tube, or on portions of both the outer and corresponding inner surfaces of the tube. For example a longitudinal portion of the tube on one side of the tube may be coated with the water swellable material. In some cases, 50% of the tube or less is coated with the water swellable material, such as 40% or less, or 30% or less, or 25% or less, or 20% or less or 15% or less, or 10% or less of a longitudinal portion of the tube is coated with the water swellable material. As described above, in embodiments where a portion of the tube is coated with the water swellable material, localized swelling on a portion of the tube may place the tube into a curved configuration (e.g., the second configuration as described herein). In some cases, the inner tube is less hydrophilic than the water swellable material, such that the water swellable material facilitates localized swelling on the portion of the tube where the water swellable material is disposed, and as such places the tube in a desired curved configuration. See FIGS. 11A and 11B. The water swellable material may be coated onto an outer surface of the inner tube, such as by being laminated to the inner tube, or may be attached to the inner tube using an adhesive. In some instances, swelling of the water swellable material does not cause delamination of the water swellable material from the inner tube.

In some embodiments, the tube is composed of the water swellable material. For example, a portion of the tube (e.g., one side of the tube) is composed of the water swellable material. For example a longitudinal portion of the tube on one side of the tube may be composed of the water swellable material. In some cases, 50% of the tube or less is composed of the water swellable material, such as 40% or less, or 30% or less, or 25% or less, or 20% or less or 15% or less, or 10% or less of a longitudinal portion of the tube is composed of the water swellable material. As described above, in embodiments where a portion of the tube is composed of the water swellable material, localized swelling of the water swellable portion of the tube may place the tube into a curved configuration (e.g., the second configuration as described herein).

The water swellable material may be a material such as, but not limited to, a water insoluble hydrophilic polymer. As used herein, a water swellable material is a composition which when exposed to water absorbs 20 weight percent or more, 35 weight percent or more, 50 weight percent or more, 60 weight percent or more, 75 weight percent or more, 90 weight percent or more, or 100 weight percent or more water from the surrounding environment. Examples of a water swellable material include a water insoluble hydrophilic polymer, such as, but are not limited to, aliphatic polyether polyurethanes such as Tecophilic® polymers (Lubrizol Advanced Materials, Wilmington, Mass.), ethylene vinyl acetate, cellulose acetate, cross linked polyvinyl pyrrolidone, cross linked sodium carboyxmethyl cellulose, cross linked gelatin, cross linked poly acrylic acid, cross linked hydroxyethyl methacrylate, cross linked hydroxyethyl cellulose, cross linked carboxymethyl starch, cross linked alginic acid, cross linked tragacanth, cross linked xanthan gum, cross linked carrageenan, and like, and combinations thereof.

In certain embodiments, the tube includes a tip at its distal end configured to facilitate insertion of the tube into the stenotic opening of the paranasal sinus of the subject. The tip may be secured, either removably or permanently, to either the tube or, optionally to the protective sheath if present, or both. In some cases, the tip includes a pointed distal tip which extends distally beyond the distal end of the tube, thus facilitating penetration of the tube through the tissue of the subject.

In certain embodiments, the distal end of the tube is positioned at an angle of 0° to 150° relative to the longitudinal axis of the hollow elongated member, such as 10° to 150°, including 20° to 150°, or 30° to 150°, or 30° to 150°, or 45° to 150°, or 60° to 150°, or 60° to 120°, or 90° to 120°, or 100° to 120°, or 105° to 115°, relative to the longitudinal axis of the hollow elongated member. In some instances, the distal end of the tube is positioned at an angle of 110° relative to the longitudinal axis of the hollow elongated member. In certain embodiments, an insertion device having a distal end with an angle of 110° may facilitate insertion of the tube into a paranasal sinus (e.g., a maxillary sinus) of a patient. In some instances, the distal end of the tube is positioned at an angle of 70° relative to the longitudinal axis of the hollow elongated member. In certain embodiments, an insertion device having a distal end with an angle of 70° may facilitate insertion of a sinus dilator into a paranasal sinus (e.g., a maxillary sinus) of a patient, such as insertion of a sinus dilator through the tube and into a paranasal sinus of the patient.

In certain embodiments, the shape-memory material of the tube is configured to have an angle relative to the longitudinal axis of the hollow elongated member as described above. The tube may have an initial configuration where the longitudinal axis of the tube is substantially aligned with the longitudinal axis of the hollow elongated member. For instance, the tube may be engaged to the distal end of the hollow elongated member, such as surrounding the outside surface of the hollow elongated member. During use, the tube may be extended from the distal end of the hollow elongated member. For example, the tube may be slidably engaged to the distal end of the hollow elongated member, and thus may be deployed from the hollow elongated member by sliding the tube over the hollow elongated member in a distal direction. In other embodiments, the tube may be contained within the hollow elongated member. In these embodiments, the tube may be extended from the distal end of the hollow elongated member by sliding the tube in a distal direction from the hollow elongated member such that the tube is extended a distance beyond the distal end of the hollow elongated member.

In certain embodiments, the tube is composed of a shape-memory material as described above. In its initial configuration, the longitudinal axis of the tube is substantially aligned with the longitudinal axis of the hollow elongated member as described above. Upon deployment of the tube from the distal end of the hollow elongated member, the shape-memory material may be configured to conform to a second shape (e.g., the second configuration). For instance, the shape-memory material may be configured to conform to a shape where the distal end of the tube is positioned at an angle relative to the longitudinal axis of the hollow elongated member. As described above, the angle of the distal end of the tube may be 0° to 150° relative to the longitudinal axis of the hollow elongated member, such as 10° to 150°, including 20° to 150°, or 30° to 150°, or 30° to 150°, or 45° to 150°, or 60° to 150°, or 60° to 120°, or 90° to 120°, or 100° to 120°, or 105° to 115°, relative to the longitudinal axis of the hollow elongated member. In some instances, the shape-memory material may be configured to conform to a second shape where the distal end of the tube is positioned at an angle of 110° relative to the longitudinal axis of the hollow elongated member. In certain embodiments, second shape where the distal end is positioned at an angle of 110° may facilitate insertion of the tube into a paranasal sinus (e.g., a maxillary sinus) of a patient. In some instances, the shape-memory material may be configured to conform to a second shape where distal end of the tube is positioned at an angle of 70° relative to the longitudinal axis of the hollow elongated member. In certain embodiments, second shape there the distal end is positioned at an angle of 70° may facilitate insertion of a sinus dilator into a paranasal sinus (e.g., a maxillary sinus) of a patient, such as insertion of a sinus dilator through the tube and into a paranasal sinus of the patient.

The curvature and length of curvature of the tube may vary in degree, and may vary according to application, such as with which sinus opening is being accessed, e.g., maxillary sinus, frontal sinus, sphenoid sinus, etc. In some cases, the length of the curved section of the tube (e.g., the arc length of the curved section) is 5 cm or less, such as 3 cm or less, including 2 cm or less, or 1 cm or less, or 0.5 cm or less.

In certain embodiments, the tube is radially expandable. By "radially expandable" is meant that the tube has an initial diameter and is configured to be capable of changing from the initial diameter to a configuration with a diameter greater than the initial diameter. For example, the tube may have a relatively small initial diameter configured to facilitate insertion of the tube into a stenotic opening of a paranasal sinus of a subject. After insertion of the tube into the stenotic opening of the paranasal sinus of the subject, the tube may be expanded into a configuration having a greater diameter than the initial diameter to facilitate insertion of a sinus dilator into the stenotic opening as described herein. For instance, after the tube is inserted into the stenotic opening, the sinus dilator may be inserted through the tube into the stenotic opening. As the sinus dilator traverses through the tube, the diameter of the tube may expand from the initial diameter to a greater diameter to accommodate the sinus dilator. As such, the tube may be configured to facilitate placement of the sinus dilator within the stenotic opening.

In some instances, the tube is configured to be inserted into a stenotic opening of a paranasal sinus of a subject. For example, the tube may have an initial (e.g., un-expanded) diameter ranging from 1 mm to 5 mm, such as 1 mm to 4 mm, including 1 mm to 3 mm, or 1 mm to 2 mm. After insertion of the tube into the stenotic opening of the paranasal sinus of the subject, the tube may be expanded to a greater diameter, such as an expanded diameter ranging from 1 mm to 15 mm, or from 1 mm to 12 mm, or from 1 mm to 10 mm, or from 1 mm to 7 mm, or from 1 mm to 5 mm, or from 1 mm to 4 mm, or from 1 mm to 3 mm, or from 1 mm to 2 mm. In certain cases, the expanded tube will define an access lumen from the nasal cavity to the desired paranasal sinus, and may facilitate insertion of the sinus dilator into the stenotic opening of the paranasal sinus of the subject.

In certain embodiments, the tube includes an elongated tube having a distal end, a proximal end, and an axial lumen extending from the distal end to the proximal end. In some cases, the tube includes an expandable tubular braid which may be initially in an elongated, narrow-diameter configuration. The tube may be initially deployed in its narrow-diameter configuration, and thereafter expanded to a configuration having a diameter greater than in the initial configuration. In certain instances, the tube is formed as a mesh of individual filaments so that radial expansion causes axial shortening of the tube. In some instances, such axial shortening as the braid filaments are radially penetrated into the surrounding tissue helps anchor the tube in place within the patient's tissue.

The overall weight of the insertion device may take into account usability as a handheld device by the user, e.g., to permit a physician to easily hold and handle the device during an insertion procedure. The shape of the handheld member may vary, but in some instances may be in the shape of a wand with a button or switch trigger, a gun-like handle and trigger, or other graspable and usable shape.

As summarized above, the insertion device is dimensioned such that at least the distal end of the device can pass through the nasal cavity of a subject. The distal end may include, for example, at least a portion of the hollow elongated member, interior elongated member and retention interface. As such, at least the distal end of the device has a cross-sectional diameter that is 10 mm or less, such as 8 mm or less, and including 5 mm or less. The elongated members may have the same outer cross-sectional dimensions (e.g., diameter) along its entire length. Alternatively, the cross-sectional diameter may vary along the length of the elongated members.

Furthermore, the lengths of the hollow elongated member and interior elongated member may vary. For example, the lengths of the elongated members may vary depending on the specific sinus being targeted. In some instances, the lengths of the elongated members range from 1 cm to 20 cm, such as 2 cm to 15 cm, including 5 cm to 10 cm. It should be appreciated that in some instances the hollow elongated member and interior elongated member may have different lengths from one another.

As stated above, the hollow elongated member and interior elongated member of the insertion device has a proximal end and a distal end. The term "proximal end", as used herein, refers to the end of the elongated members (or the insertion device or other component on the insertion device) that are nearer the user (such as a physician operating the device in an insertion procedure), and the term "distal end", as used herein, refers to the end of the elongated members (or the insertion device or other component on the insertion device) that are nearer the target stenotic opening of the subject during use.

The hollow elongated member may be, for example, a structure of sufficient rigidity to allow the distal end to be pushed through tissue when sufficient force is applied to the proximal end of the device. In some cases, the hollow elongated member has sufficient rigidity to maintain the tube in its first configuration as described above when the tube is concentrically aligned with the hollow elongated member. As such, in some embodiments, the hollow elongated member is not pliant or flexible, at least not to any significant extent. Example materials may include, but are not limited to, metals, metal alloys (e.g., stainless steel), polymers such as hard plastics, etc.

The interior elongated member may be, in some instances, a structure of sufficient rigidity to allow the sinus dilator to be pushed through the stenotic opening when sufficient force is applied to the proximal end of the device, even when the stenotic opening is completely occluded. In some instances, the interior elongated member may be a metal, metal alloy, polymer (hard or pliant and flexible), etc. Further, the interior elongated member is, in some instances, a structure sufficiently pliant and flexible such that the interior elongated member may be relatively displaced in a tube having a curved tip section. Examples of sufficiently pliant and flexible materials may include, but are not limited to, polymers such as plastics, rubber-like polymers, flexible metal (e.g., flexible wire), etc. In such cases, the hollow elongated member may provide the rigidity necessary to push the sinus dilator through the stenotic opening with sufficient force applied to the proximal end of the device.

As summarized above, the insertion device may include an interface (e.g., a retention interface) adapted to removably couple to the sinus dilator. For example, the interface may be configured to mate with (e.g., slide within), clamp on, or removably couple in another way with, the sinus dilator. In some instances, the interface is part of the interior elongated member in that the retention interface and interior elongated member are parts of a single unitary piece of material. In some cases, the interface is part of the tube in that the retention interface and the tube are parts of a single unitary piece of material. In other instances, the interface may be a separate piece of material that is coupled to the interior elongated member or the tube, either removably or non-removably coupled in different embodiments. Retention interfaces that are removably coupled to the insertion device may provide the ability to replace retention interfaces (e.g., for sanitation purposes, or replacement purposes) or switch to different types of retention interfaces (e.g., for use with different types or sized sinus dilators).

In some embodiments, the interface is adapted to fit within a central passageway of the sinus dilator. The interface may be, for example, shaped and sized to fit within the contours of the central passageway of the sinus dilator. The sinus dilator may then be coupled to the interface by sliding the sinus dilator onto the interface. In some instance, the shape and size of the interface matches the contours of the central passageway of the sinus dilator. Also, in some instances, the interface may be slid all the way through the central passageway of the sinus dilator with a tip portion extending out of the sinus dilator. In other embodiments, the interface contacts the proximal end of the sinus dilator without being inserted within the sinus dilator. For example, the interface may be located at the distal end of the interior elongated member and may contact the proximal end of the sinus dilator. As described above, actuation of the interior elongated member may correspondingly displace the sinus dilator distally or proximally with respect to the hollow elongated member.

In some embodiments, the interface includes retaining elements that provide an additional securing force to the sinus dilator so that the sinus dilator remains coupled to the interface unless a sufficient amount of force is applied to overcome the additional securing force, or until the additional securing force is removed. For example, the interface may, for instance, include a compressible lip, bump, or other protrusion that fit within mating recesses on the sinus dilator that "snap" the dilator onto the interface. Sufficient force to overcome the additional securing force by the retaining elements may be provided by, for example, withdrawing the interior elongated member while the sinus dilator is securely fit within the stenotic opening. As another example, the sufficient force may be provided by the interior elongated member being displaced and pushed into the sinus dilator to push the sinus dilator off the interface, for example where the interface is located on the distal end of the tube. It should be appreciated that the size and shape of the protrusions will determine the amount of sufficient force necessary to overcome the additional securing force provided by the protrusions.

In some embodiments, the insertion device may include a lumen that extends to the distal end of the insertion device. For example, the lumen may extend within the interior elongated member and include an opening at the distal tip of the elongated member. It should be appreciated that the lumen may, in some instances, be formed by the interior elongated member or formed by a tube positioned within the interior elongated member. In alternative embodiments, the lumen may be positioned within the hollow elongated member but not within the interior elongated member.

In some instances, insertion device is configured to couple the lumen to a fluid source to dispense fluid into the sinus cavity or nasal cavity before, during or after placement of the sinus dilator in the stenotic opening. The term "fluid" is used herein generally to refer to any variety of fluids, mists, gels, single or multi-phase liquid, etc., or combinations thereof. The fluid source may be located in various positions, depending on design, e.g., being located on or in the device, attaching to the device (e.g., a cartridge, etc.), or coupling to the device via a connection port, etc. In some instances, the lumen is coupled to a hollow tube in the handheld member that brings the lumen in fluid communication with the fluid source. Example fluids that may be dispensed are, for example, fluids comprising water, saline solution, drugs, etc. Example drugs that may be present in the fluid (e.g., in fluid or solid form) may include, but are not limited to fluids comprising one or more analgesics, anesthetics, anti-inflammatories, antibiotics, steroids, drugs that control or limit bleeding (e.g., vasoconstrictors), etc.). Vasoconstrictors may include, for example, oxymetazoline, epinephrine, tranexamic acid, salts thereof, combinations thereof, and the like.

In some embodiments, the lumen may be coupled to a pellet source or other source of solid, such as powder, etc. In such case, the lumen is used to dispense solid pellets, for example, into the sinus cavity and/or nasal cavity before, during or after placement of the sinus dilator in the stenotic opening. Furthermore, in some instances, the lumen may be coupled to a suction source (e.g., vacuum source) in order to provide suctioning, in order to remove fluid, tissue debris, etc. It should be appreciated that in some instances more than one lumen may be implemented. For example, in some instances, one lumen may be provided to dispense fluids while another lumen is provided for suctioning purposes.

In some embodiments, the insertion device may be configured to include a camera positioned near the distal end of the hollow elongated member in order to assist in visualizing the stenotic site, nasal cavity, or sinus cavity. In some instances, the camera may be positioned on the exterior surface of the hollow elongated member and, for example, electrically coupled to a monitor via an electrical wire extending along or within the hollow elongated member. In other instances, the camera may be positioned within the hollow elongated member. For example, a camera may be positioned at the tip of the interior elongated member and electrically coupled to a monitor via an electrical wire extending within the interior elongated member.

The insertion device, or components thereof, may be configured for one time use (i.e., disposable) or may be re-usable, e.g., where the components are configured to be used two or more times before disposal, e.g., where the device components are sterilizable.

Referring now to FIG. 1, there is shown a human patient 10 having two frontal sinuses (FS) and two maxillary sinuses (MS). Each of these four sinuses has an opening which can be accessed by way of the patient's nostrils. The openings include maxillary sinus openings 11 and 12, of which opening 11 is shown in a normal open condition and opening 12 shown in an occluded or stenotic condition. Similarly, the patient 10 has frontal sinus openings 13 and 14, of which opening 14 is shown in a normal open condition and opening 13 is shown in an occluded or stenotic condition.

Figure 2:
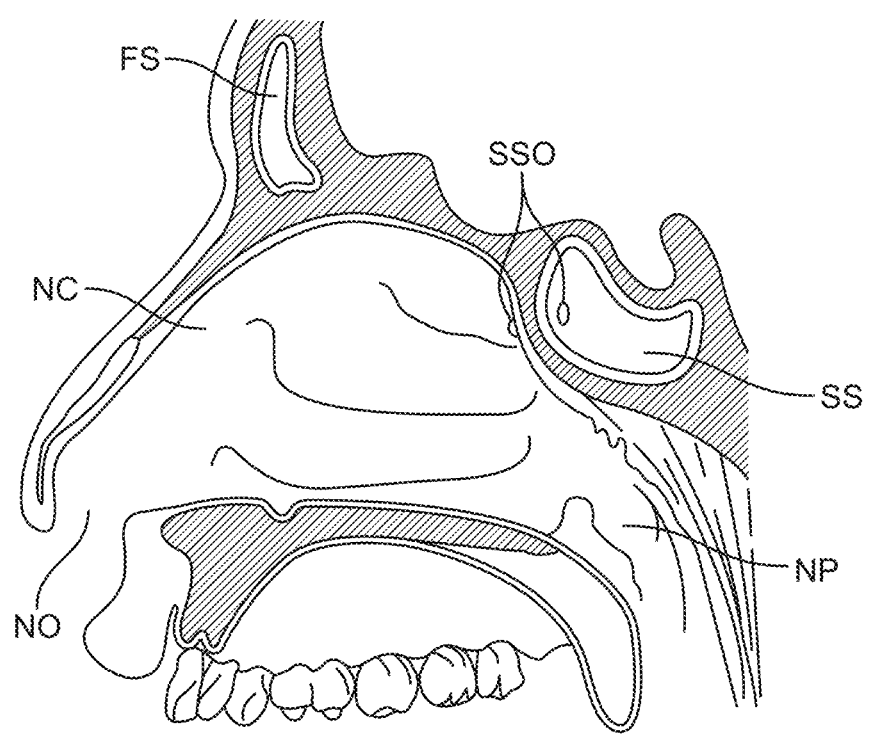
FIG. 2 shows a sectional view of a portion of a human head showing the positions of the frontal sinus (FS) and the sphenoid sinus (SS).

Referring now to FIG. 2, there is shown a sectional view of a patient's nose and sinuses including the nasal cavity (NC), the nasopharynx (NP), the nostril opening (NO), the frontal sinus (FS), the sphenoid sinus (SS) and the sphenoid sinus opening (SSO).

Figure 3:
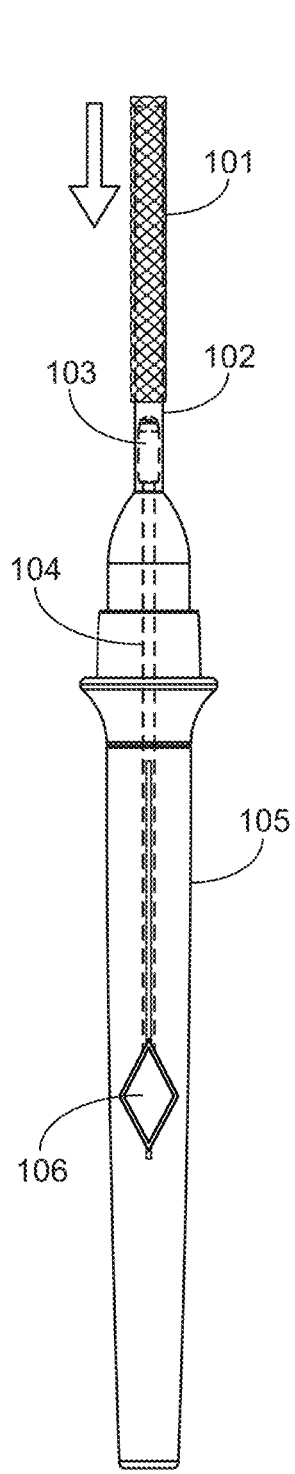
FIG. 3 shows a side view of an insertion device according to embodiments of the present disclosure.

FIG. 3 shows a side view of an insertion device. The insertion device includes a tube 101 slidably engaged to the hollow elongated member 102 of the insertion device. As shown in FIG. 3, the tube 101 is configured to surround at least the distal portion of the hollow elongated member 102. In other embodiments, the tube may be configured to be slidably engaged to the inside of the hollow elongated member such that the tube may be deployed from the device from within the hollow elongated member. As shown in FIG. 3, the insertion device also includes a sinus dilator 103 removably coupled to the distal end of the interior elongated member 104. The interior elongated member 104 extends within the interior cavity of the hollow elongated member 102 and is operatively coupled to an actuator 106. The insertion device also includes a handle 105 configured to be held by a user's hand. The actuator 106 is positioned on the handle 105, such that the actuator 106 may be activated by a thumb or finger of the user.

Figure 4:
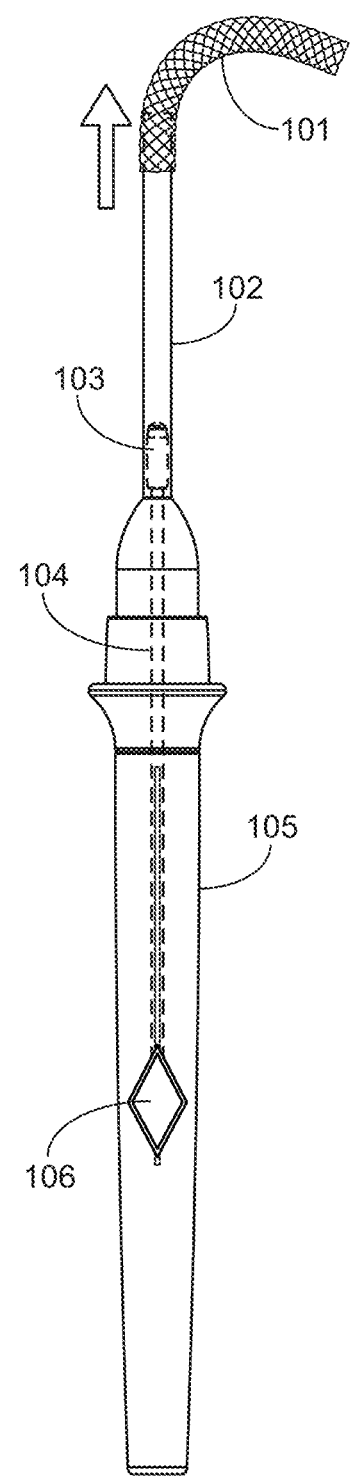
FIG. 4 shows a side view of an insertion device with a tube extended from the distal end of the insertion device according to embodiments of the present disclosure.

FIG. 4 shows a side view of an insertion device with the tube 101 extended from the distal end of the insertion device. The tube may be extended from the distal end of the hollow elongated member 102 such that only a portion of the proximal end of the tube 101 remains in contact with the distal end of the hollow elongated member 102. In some cases, the insertion device includes a second actuator (not shown) operatively coupled to the tube 101, such that activation of the second actuator controls the position of the tube 101 relative to the hollow elongated member 102. For instance, activation of the second actuator in a distal direction may result in deployment and extension of the tube 101 from the distal end of the hollow elongated member 102. Similarly, activation of the second actuator in a proximal direction may result in retraction of the tube 101.

As disclosed herein, the tube 101 may be composed of a shape-memory material (e.g., shape-memory alloy or shape-memory polymer). In these embodiments, the tube 101 may be configured to conform to a shape that is different from its shape when the tube 101 surrounds the hollow elongated member as shown in FIG. 3. For example, as shown in FIG. 3, when the tube 101 is positioned such that the hollow elongated member 102 is within the tube 101, the tube 101 may be maintained in a substantially straight configuration such that the longitudinal axis of the tube 101 is substantially aligned with the longitudinal axis of the hollow elongated member 102.

As shown in FIG. 4, when the tube 101 composed of a shape-memory material is extended from the end of the hollow elongated member 102, the shape-memory material may conform to a different shape (e.g., a second configuration) such that the distal end of the tube 101 is positioned at an angle relative to the hollow elongated member 102. Stated another way, the tube 101 may conform to a curved (e.g., bent) configuration such that distal tip of the tube 101 has an axial direction at an angle relative to the axial direction of the distal tip of the hollow elongated member 102. As described herein, the distal end of the tube 101 may be positioned at an angle of 0° to 150° relative to the longitudinal axis of the hollow elongated member 102, such as 10° to 150°, including 20° to 150°, or 30° to 150°, or 30° to 150°, or 45° to 150°, or 60° to 150°, or 60° to 120°, or 90° to 120°, or 100° to 120°, or 105° to 115°, relative to the longitudinal axis of the hollow elongated member 102. For instance, the angle may be 110° as shown in FIG. 4, or in other instances may be 70° (see, e.g., FIG. 6).

Figure 5:
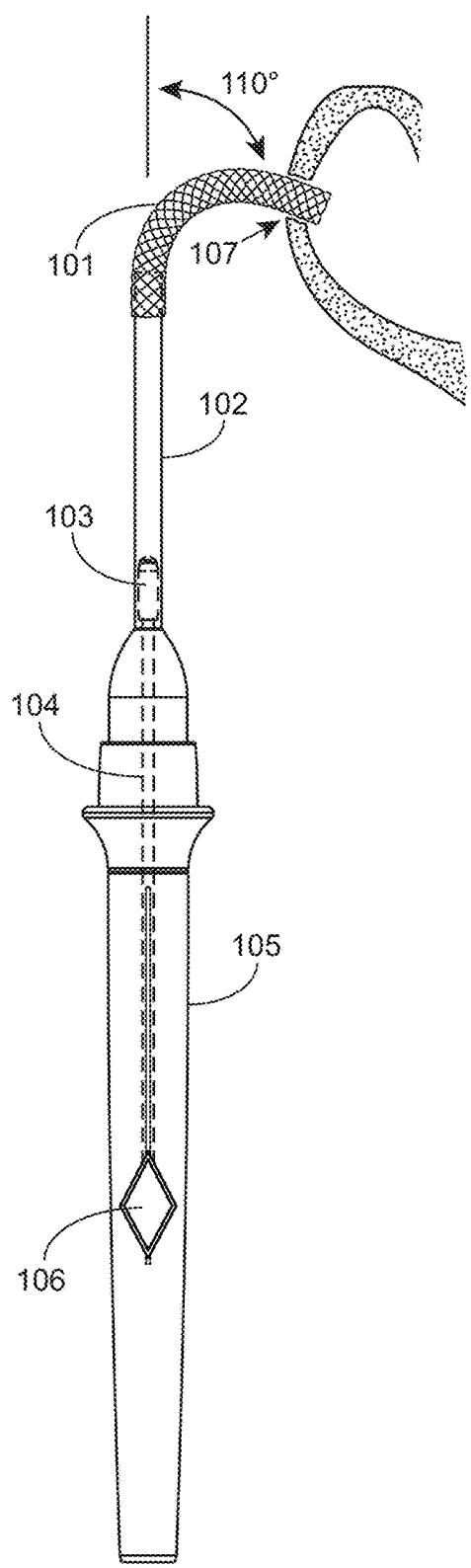
FIG. 5 shows a side view of an insertion device with the tube extended from the distal end of the device at 110° to facilitate insertion of the tube into a stenotic opening of a paranasal sinus in a subject, according to embodiments of the present disclosure.

As shown in FIG. 5, an insertion device having a distal end with an angle of 110° may facilitate insertion of the tube 101 into a stenotic opening 107 of a paranasal sinus (e.g., a maxillary sinus) of a patient. In some instances, when the tube 101 is extended from the distal end of the insertion device, the tube 101 has an initial diameter (e.g., an un-expanded diameter) that is less than the expanded diameter of the tube 101. After insertion of the tube 101 into the stenotic opening 107 of the paranasal sinus of the subject, the tube 101 may be expanded to a greater diameter to facilitate insertion of the sinus dilator 103 into the stenotic opening 107 of the paranasal sinus of the subject.

Figure 6:
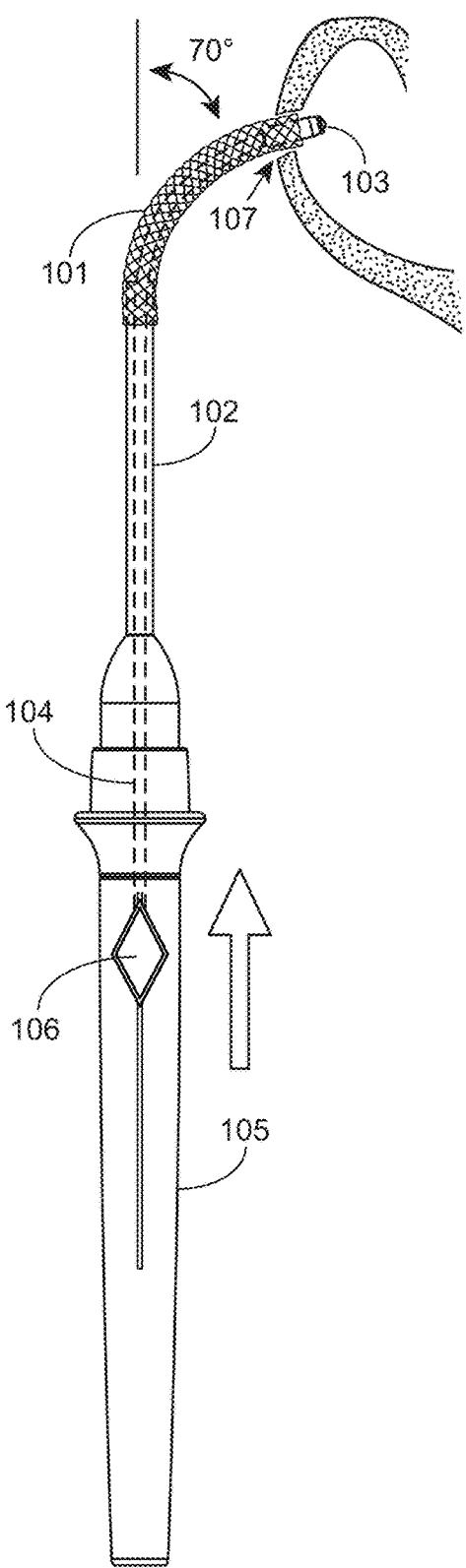
FIG. 6 shows a side view of an insertion device with the tube extended from the distal end of the device at 70° to facilitate insertion of a sinus dilator through the tube into the stenotic opening of a paranasal sinus in a subject, according to embodiments of the present disclosure.

As shown in FIG. 6, the actuator 106 may be activated in a distal direction. As described above, the actuator 106 is operatively coupled to the interior elongated member 104, such that activation of the actuator 106 in a distal direction results in a corresponding movement of the interior elongated member 104 in a distal direction. As such, the sinus dilator 103 coupled to the distal end of the interior elongated member 104 may be advanced in a distal direction through the hollow elongated member 102 and through the tube 101. In some instances, the sinus dilator 103 may have an outside diameter that is greater than the initial (e.g., un-expanded) diameter of the tube 101. In these embodiments, passage of the sinus dilator 103 through the tube 101 may cause the tube 101 to expand in diameter to accommodate the sinus dilator 103.

Also shown in FIG. 6, the distal end of the tube 101 may be positioned at an angle of 70° relative to the longitudinal axis of the hollow elongated member 102, which may facilitate insertion of the sinus dilator 103 into the stenotic opening 107 of the paranasal sinus.

Figure 7:
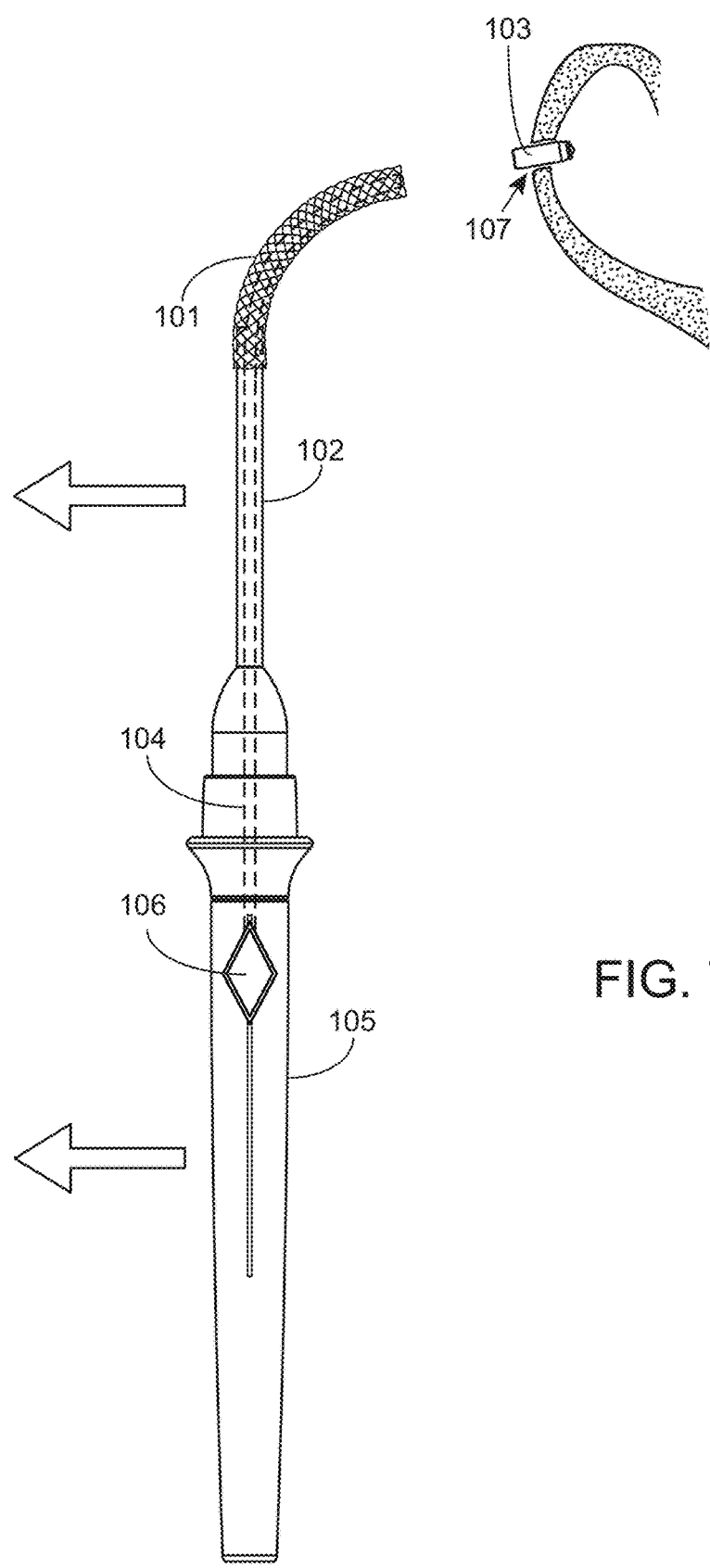
FIG. 7 shows a side view of an insertion device with the tube removed from the stenotic opening, leaving the sinus dilator in place, according to embodiments of the present disclosure.

As shown in FIG. 7, after insertion of the sinus dilator 103 into the stenotic opening 107, the tube 101 may be removed from the stenotic opening 107, leaving the sinus dilator 103 in the stenotic opening 107. The insertion device may then be removed from the nasal cavity of the subject.

Figure 8:
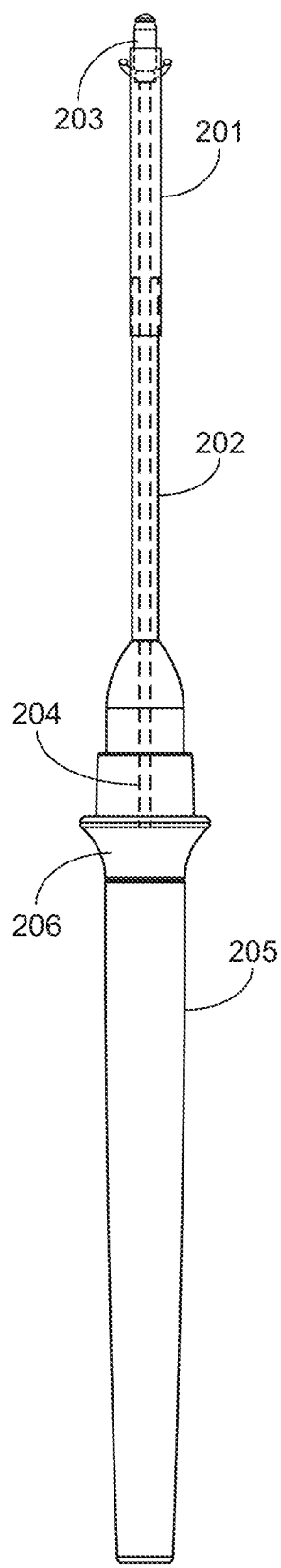
FIG. 8 shows a side view of an insertion device according to embodiments of the present disclosure.

FIG. 8 shows a side view of an embodiment of insertion device according to the present disclosure. The insertion device includes a tube 201 engaged to the hollow elongated member 202 of the insertion device. As shown in FIG. 8, the tube 201 is configured to surround at least a distal portion of the hollow elongated member 202. In other embodiments, the tube may be configured to be engaged to the inside of the hollow elongated member. As shown in FIG. 8, the insertion device also includes a sinus dilator 203 removably coupled to the distal end of the interior elongated member 204. The interior elongated member 204 extends within the interior cavity of the hollow elongated member 202 and is operatively coupled to an actuator 206. The insertion device also includes a handle 205 configured to be held by a user's hand. The actuator 206 is positioned on the handle 205, such that the actuator 206 may be activated by a thumb or finger of the user.

As disclosed herein, the tube 201 may be composed of a water swellable material. In these embodiments, the tube 201 may be configured such that a portion of the tube is coated with or composed of the water swellable material. For example, one side of the tube may be coated with or composed of the water swellable material as described herein. As shown in FIG. 8, before insertion the tube 201 is configured such that the tube 201 is in a substantially straight configuration such that the longitudinal axis of the tube 2 substantially aligned with the longitudinal axis of the hollow elongated member 202.

Figure 9:
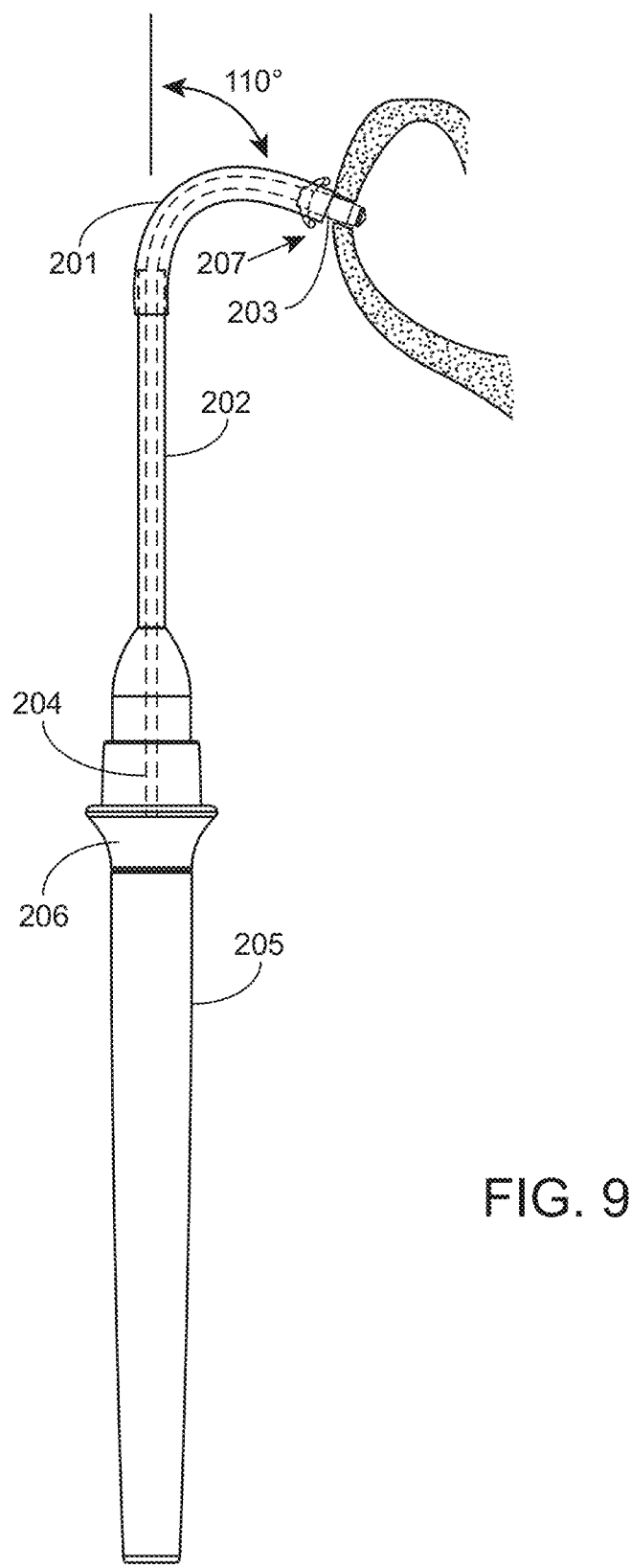
FIG. 9 shows a side view of an insertion device with the tube extended from the distal end of the device at 110° to facilitate insertion of the tube into a stenotic opening of a paranasal sinus in a subject, according to embodiments of the present disclosure.

As shown in FIG. 9, when the tube 201 is inserted into the nasal cavity of a subject, the water swellable material may absorb water from the surrounding tissues of the subject. Subsequent swelling of the water swellable material may cause tube 201 to conform to a different shape (e.g., a second configuration) such that the distal end of the tube 201 is positioned at an angle relative to the hollow elongated member 202. Stated another way, the tube 201 may conform to a curved (e.g., bent) configuration such that distal tip of the tube 201 has an axial direction at an angle relative to the longitudinal axis of the hollow elongated member 202. As described herein, the distal end of the tube 201 may be positioned at an angle of 0° to 150° relative to the longitudinal axis of the hollow elongated member 202, such as 10° to 150°, including 20° to 150°, or 30° to 150°, or 30° to 150°, or 45° to 150°, or 60° to 150°, or 60° to 120°, or 90° to 120°, or 100° to 120°, or 105° to 115°, relative to the longitudinal axis of the hollow elongated member 202. For instance, the angle may be 110° as shown in FIG. 9, or in other instances may be 70° (see, e.g., FIG. 6).

As shown in FIG. 9, an insertion device having a distal end with an angle of 110° may facilitate insertion of the tube 201 into a stenotic opening 207 of a paranasal sinus (e.g., a maxillary sinus) of a patient. As shown in FIG. 9, the tube 201 has a sinus dilator 203 removably coupled to the distal end of the tube 201. In some instances, the bent configuration of the tube 201 facilitates insertion of the sinus dilator 203 into the stenotic opening 207 of the paranasal sinus of the subject.

Figure 10:
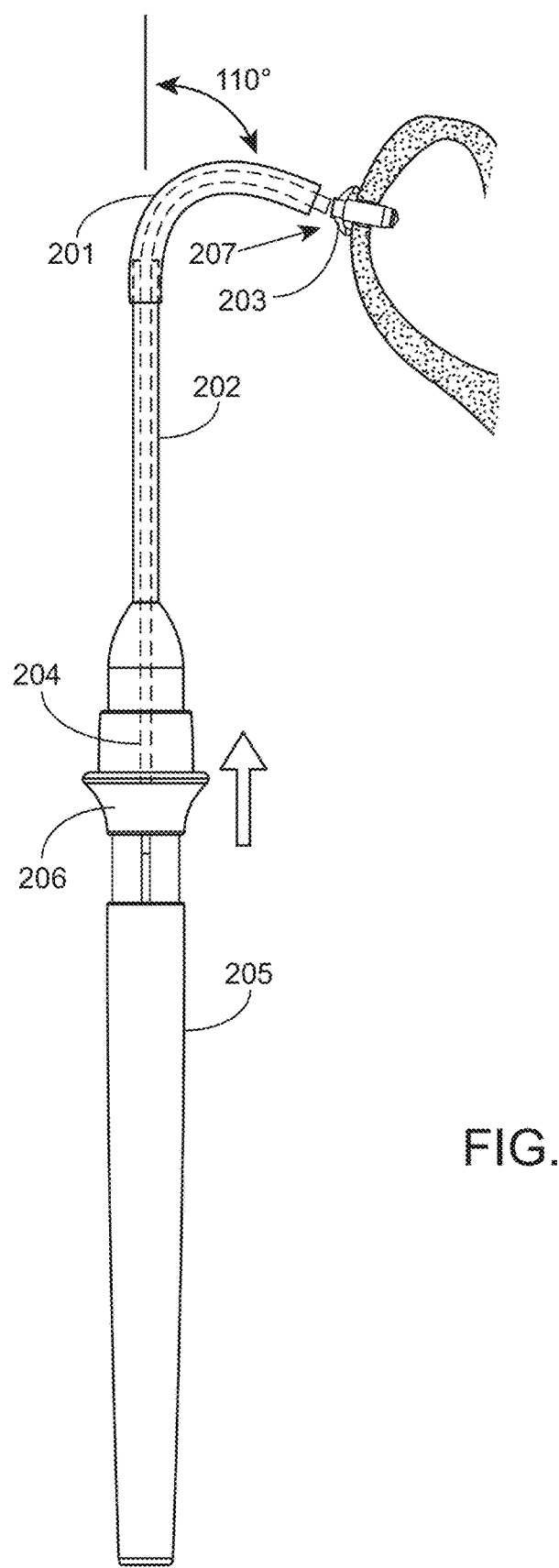
FIG. 10 shows a side view of an insertion device after insertion of the sinus dilator in a stenotic opening of a subject, according to embodiments of the present disclosure.

As shown in FIG. 10, the actuator 206 may be activated in a distal direction. As described above, the actuator 206 is operatively coupled to the interior elongated member 204, such that activation of the actuator 206 in a distal direction results in a corresponding movement of the interior elongated member 204 in a distal direction. After the sinus dilator 203 is positioned in the stenotic opening 207 of the subject, the sinus dilator 203 coupled to the distal end of the tube 201 may be decoupled from the tube 201 as described above. After insertion of the sinus dilator 203 into the stenotic opening 207, the tube 201 and insertion device may be removed from the nasal cavity of the subject, leaving the sinus dilator 203 in the stenotic opening 207.

Additional aspects of the insertion devices and methods for use are also described in U.S. patent application Ser. Nos. 13/219,505 and 13/219,497, both filed Aug. 26, 2011, and U.S. patent application Ser. No. 13/777,748, filed Feb. 26, 2013, the disclosures of each of which are incorporated herein by reference.

Devices and Methods for Dilating a Stenotic Opening of a Paranasal Sinus in a Subject Aspects of the present disclosure include devices and methods for dilating a stenotic opening of a paranasal sinus in a subject. The device (e.g., sinus dilator) includes an expandable portion configured to expand from a non-expanded configuration to an expanded configuration, where the non-expanded configuration is sized to be positioned within the stenotic opening, and a driver configured to expand the expandable portion from the non-expanded configuration to the expanded configuration, where the expanded configuration dilates the stenotic opening.

The term "stenotic opening" refers to an abnormal narrowing of a biological passageway, such as a paranasal sinus opening. In certain embodiments, the device includes an osmotic driver configured to expand an expandable portion from a non-expanded configuration to an expanded configuration, and the expandable portion disposed peripherally around the driver and configured to expand from the non-expanded configuration to the expanded configuration, where the non-expanded configuration is sized to be positioned within the stenotic opening.

In certain embodiments, the driver is self-expanding when in contact with tissue of the subject. By "self-expanding" is meant that the driver may expand from the non-expanded configuration to the expanded configuration without external intervention from a user or a health care practitioner. For example, the self-expanding driver may be self-contained, such that the driver is configured to expand without connection to an external pressure source. As such, self-expanding drivers as described herein function without the need for an external pressure source or a pressure monitoring device (e.g., as with a balloon catheter). In some cases, the self-expanding driver expands from the non-expanded configuration to the expanded configuration upon absorbing fluid from the surrounding environment when the device is in use. For instance, the self-expanding driver may expand from the non-expanded configuration to the expanded configuration upon absorbing water from the surrounding tissues of the stenotic opening when the device is in use. Self-expanding drivers may be configured to expand the expandable portion of the device by various ways, such as, but not limited to, an osmotic agent, a swellable agent (e.g., a swellable polymer), combinations thereof, and the like. In some instances, the driver is configured to expand the expandable portion by at least one of osmosis, a shape memory metal, a spring, a swellable polymer, a thermal expansion of a gas, a thermal expansion of a liquid, a gas-generating chemical reaction and a phase change expansion of a material.

In certain embodiments, the driver includes an osmotic agent. As used herein, the terms "osmotic agent," "osmotically active agent" and "osmoagent" are used interchangeably and refer to an agent that facilitates the imbibition of water from a region of high water potential (e.g., low solute concentration) through a semipermeable membrane to a region of low water potential (e.g., high solute concentration) until a state of dynamic equilibrium is reached. In some instances, the osmotically active agent may be configured to absorb water flowing through a semipermeable membrane from the surrounding tissues after insertion of the device into the stenotic opening of the subject and expand. In certain embodiments, the osmotic agent is configured to have a zero order rate of expansion. By "zero order" is meant that the rate of volume expansion of the osmotic agent is approximately constant over time and is independent of the surrounding solute concentration.

In certain embodiments, the driver is configured to begin expanding upon insertion of the device into the stenotic opening of the subject. The terms "insert" or "insertion" are used herein interchangeably to describe the positioning of a device in a stenotic opening of a subject for a period of time. In some instances, the driver is configured to begin expanding within seconds or minutes after insertion of the device into the stenotic opening. In some cases, the driver is configured to begin expanding in 60 min or less, such as 45 min or less, or 30 min or less, including 10 min or less, or 5 min or less, such as 1 min or less, after insertion of the device into the stenotic opening. In some instances, the driver is configured to continue to expand for a certain period of time after the device has been inserted into the stenotic opening of the subject. For example, the driver may be configured to continue to expand for 30 min or more, such as 45 min or more, including 60 min or more, or 90 min or more, 120 min or more, or 180 min or more, or 240 min or more, or 300 min or more after the device has been inserted into the stenotic opening of the subject.

In certain embodiments, the driver takes a certain amount of time to expand the expandable portion from the non-expanded configuration to the expanded configuration. For instance, in some cases the driver is configured to expand the expandable portion from the non-expanded configuration to the expanded configuration over a period of 0.5 hours or more, such as 1 hour or more, or 2 hours or more, or 4 hours or more, or 6 hours or more, or 8 hours or more, or 10 hours or more, or 12 hours or more, or 24 hours or more, or 48 hours or more, or 72 hours or more, etc. In some instances, the driver is configured to expand the expandable portion from the non-expanded configuration to the expanded configuration over a period of 24 hours or less, such as 12 hours or less, or 10 hours or less, or 8 hours or less, or 6 hours or less, or 4 hours or less, or 2 hours or less, 1.5 hours or less, or 1 hours or less, or 0.5 hours or less. As such, in certain instances, the driver is configured to expand the expandable portion from the non-expanded configuration to the expanded configuration over a period ranging from 0.5 hours to 24 hours, such as 0.5 hour to 12 hours, including 0.5 hour to 10 hours, or 1 hour to 8 hours, or 1 hour to 6 hours, or 1 hour to 4 hours, or 1 hour to 2 hours.

In certain embodiments, the driver is configured to expand the expandable portion to a diameter of 10 mm or less, such as 9 mm or less, or 8 mm or less, or 7 mm or less, or 6 mm or less, or 5 mm or less, or 4 mm or less, or 3 mm or less, or 2 mm or less, or 1 mm or less. In some cases, the driver is configured to expand the expandable portion to a diameter of 7 mm or less.

As used herein, the term "distal" refers to the end of a device (e.g., a sinus dilator device or insertion device), or a component thereof, that is positioned towards the end of the device that is inserted through or closest to a paranasal sinus opening of the subject. For example, the distal end of a sinus dilator device is the end of the device that is inserted through the paranasal sinus opening of the subject and remains within the sinus cavity during use. A device (e.g., a sinus dilator device or insertion device), or a component thereof, may also include a proximal end. As used herein, the term "proximal" refers to the end of the device, or component thereof, which is positioned towards the end of the device that remains on the nasal cavity side of the stenotic opening or remain external to the subject during use. For example, the proximal end of a sinus dilator device is the end of the device that remains on the nasal cavity side of the stenotic opening when the sinus dilator device is positioned in the stenotic opening during use.

Embodiments of the presently disclosed devices include an expandable portion. The expandable portion is configured to expand from a non-expanded configuration to an expanded configuration. In certain embodiments, the expandable portion is configured to expand in size from a non-expanded configuration to an expanded configuration. The expandable portion may be configured to expand in size without significantly increasing in volume, such as by stretching in one or more dimensions from the non-expanded configuration. The expandable portion may be positioned peripherally around the driver. For instance, the expandable portion may be disposed on an exterior surface of the driver. In these embodiments, expansion of the underlying driver expands the expandable portion from its non-expanded configuration to its expanded configuration.

Aspects of the present disclosure include devices that have an expandable portion, where the expandable portion includes a membrane. For instance, the expandable portion may be disposed on at least a portion of the drivers, such as surrounding the outer surface of the drivers. The membrane may be an elastic membrane, such that the membrane is configured to expand from the non-expanded configuration to the expanded configuration, as described herein. In certain instances, the membrane is a semipermeable membrane. By "semipermeable" is meant a membrane that is permeable to solvent but not significantly permeable to solute across a concentration gradient, such as a membrane that allows solvent (e.g., water) molecules to pass through the membrane by osmosis from a region of low solute concentration to a region of high solute concentration until a state of dynamic equilibrium is reached. For instance, a semipermeable membrane may be configured to allow water to pass through the membrane by osmosis from a region of low solute concentration (e.g., high water potential) to a region of high solute concentration (e.g., low water potential) until a state of dynamic equilibrium is reached.

In certain embodiments, the expandable portion includes a membrane, where the membrane is an impermeable membrane. By "impermeable" is meant a membrane that is not significantly permeable to solvent or solute. Impermeable membranes do not allow significant amounts of solvent (e.g., water) or solute molecules to pass through the membrane by osmosis even in the presence of a solute concentration gradient across the membrane.

In certain embodiments, the device includes a conduit that defines an interior lumen of the device. The conduit includes a distal end configured to be in fluid communication with an interior lumen of the paranasal sinus in the subject. In some cases, the conduit may be configured to allow fluid flow between the paranasal sinus in the subject and the nasal cavity when the device is positioned within the stenotic opening. In some instances, the conduit is configured to allow fluid and/or air to flow from the paranasal sinus to the nasal cavity of the subject. For example, the conduit may be configured to facilitate drainage of fluid from the paranasal sinus in the subject to the nasal cavity when the device is positioned within the stenotic opening. In some cases, the conduit may be configured to facilitate the flow of air into and out of the paranasal sinus in the subject.

In certain embodiments, the driver is disposed on an exterior surface of the conduit. The driver may be disposed on the exterior surface of the conduit at a position between the distal end and the proximal end of the conduit. For example, the driver may be positioned between a distal anchor at the distal end of the conduit and a proximal anchor at the proximal end of the conduit. As described herein, the expandable portion may be positioned peripherally around the driver. Thus, in these embodiments, the driver is disposed between the exterior surface of the conduit and the overlying expandable portion. Expansion of the driver expands the overlying expandable portion from its non-expanded configuration to its expanded configuration.

Aspects of the driver further include embodiments where the driver completely surrounds the conduit. The driver may be disposed on the exterior surface of the conduit around the entire periphery of the conduit. In certain embodiments, the driver surrounds the conduit around the central portion of the conduit, where the distal end of the conduit may have a distal anchor and the proximal end of the conduit may have a proximal anchor, as described in more detail herein. In some instances, the driver includes one or more subunits, where each subunit is disposed on the exterior surface of the conduit. The one or more driver subunits may be positioned such that they are in contact with the adjacent one or more driver subunits. Alternatively, the one or more driver subunits may be positioned such that there is a channel between the driver subunits. In certain instances, the channel between the driver subunits extends along the exterior surface of the conduit from the distal end of the conduit to the proximal end of the conduit. The channels may be configured to allow fluid and/or air to flow between the paranasal sinus and the nasal cavity of the subject. In certain cases, the channels are configured to allow fluid and/or air to flow from the paranasal sinus to the nasal cavity of the subject. For example, the channels may be configured to facilitate drainage of fluid from the paranasal sinus in the subject to the nasal cavity when the device is positioned within the stenotic opening. In some cases, the channels may be configured to facilitate the flow of air into and out of the paranasal sinus in the subject.

In certain embodiments, the walls of the conduit are substantially rigid. The walls of the conduit may be substantially rigid, such that the conduit maintains substantially the same shape and size during use of the device. For instance, the conduit may maintain substantially the same interior diameter during use of the device. In some instances, the walls of the conduit are substantially rigid, such that pressure exerted on the exterior surface of the conduit by the driver does not significantly decrease the interior diameter of the conduit. For example, the walls of the conduit may be substantially rigid, such that the conduit is not crushed by the driver during use of the device. In some instances, the driver is configured to expand radially outward from the conduit. As discussed above, the walls of the conduit may be substantially rigid, thus expansion of the driver may be directed radially outward away from the substantially rigid walls of the conduit. Expansion of the driver radially outward from the conduit may facilitate dilation of the stenotic opening.

In certain embodiments, the walls of the conduit are substantially non-collapsible. The walls of the conduit may be substantially non-collapsible, such that the conduit is configured to maintain an opening in the conduit during use of the device. For example, the walls of the conduit may be substantially non-collapsible, such that the conduit is not crushed by the driver during use of the device. In some cases, a non-collapsible conduit maintains substantially the same shape and size during use of the device. For instance, the conduit may maintain substantially the same interior diameter during use of the device. In some instances, the walls of the conduit are substantially non-collapsible, such that pressure exerted on the exterior surface of the conduit by the driver does not significantly decrease the interior diameter of the conduit. As discussed above, the driver may be configured to expand radially outward from the conduit and, as such, the walls of the conduit may be substantially non-collapsible, such that expansion of the driver is directed radially outward away from the substantially non-collapsible walls of the conduit. Expansion of the driver radially outward from the conduit may facilitate dilation of the stenotic opening. A substantially non-collapsible conduit may be rigid, as described above, or may be flexible and adapted to bend from its original shape. In some instances, a flexible conduit facilitates insertion of the sinus dilator in a sinus ostium.

In certain instances, the conduit includes a membrane. The conduit membrane may be a semipermeable membrane. In certain instances, the conduit membrane is a non-collapsible semipermeable membrane. In some cases, the conduit membrane is a rigid semipermeable membrane. The membrane may be configured to be permeable to solvent but not significantly permeable to solute across a concentration gradient, such that the membrane allows solvent (e.g., water) molecules to pass through the membrane by osmosis from a region of low solute concentration to a region of high solute concentration until a state of dynamic equilibrium is reached. For instance, the membrane may be configured to allow water to pass through the membrane by osmosis from an interior lumen of the conduit to the surrounding driver until a state of dynamic equilibrium is reached.

In some embodiments, the device includes a conduit that includes a semipermeable membrane, a surrounding driver, and an overlying expandable portion that includes a semipermeable membrane. In these embodiments, the device may be configured to allow solvent (e.g., water) to pass through both the semipermeable expandable portion membrane by osmosis and through the semipermeable conduit membrane by osmosis. For example, the device may be configured to allow solvent to pass through the semipermeable expandable membrane from the surrounding tissues to the underlying driver, and also allow solvent to pass through the semipermeable conduit membrane from an interior lumen of the conduit to the surrounding driver.

In other embodiments, the device includes a conduit that includes a semipermeable membrane, a surrounding driver, and an overlying expandable portion that includes an impermeable membrane. In these embodiments, the device may be configured to allow solvent (e.g., water) to pass through the semipermeable conduit membrane by osmosis but not allow significant amounts of solvent (e.g., water) to pass through the impermeable expandable portion membrane. For example, the device may be configured to allow solvent to pass through the semipermeable conduit membrane from an interior lumen of the conduit to the surrounding driver, but not allow significant amount of solvent to pass through the impermeable expandable portion membrane to the driver.

In yet other embodiments, the conduit includes an impermeable material. In some cases, the impermeable material is an impermeable membrane. For instance, the device may include a conduit that includes an impermeable membrane, a surrounding driver, and an overlying expandable portion that includes a semipermeable membrane. In these embodiments, the device may be configured to allow solvent (e.g., water) to pass through the semipermeable expandable membrane by osmosis but not allow significant amounts of solvent (e.g., water) to pass through the impermeable conduit membrane. For example, the device may be configured to allow solvent to pass through the semipermeable expandable portion membrane from the surrounding tissues to the underlying driver, but not allow significant amount of solvent to pass through the impermeable conduit membrane from the interior lumen of the conduit to the surrounding driver.

In certain instances, the conduit includes a hydrophilic insoluble polymer disposed on a portion of the surface of the conduit. For example, the hydrophilic insoluble polymer may be disposed on one side of the conduit along the length of the conduit. In these embodiments, when placed in an aqueous environment (e.g., where water may be absorbed form the surround environment such as a patient's tissues), the hydrophilic polymer may absorb water in situ and increase in size (e.g., swell). In some cases, the hydrophilic polymer may swell in one or more or an axial direction, a longitudinal direction, or in both the axial and longitudinal directions. In certain instances, because the hydrophilic polymer is localized on a portion of the conduit (e.g., on one side of the conduit), the net effect of this localized swelling is to place the conduit into a curved configuration. In some cases, the resulting curved configuration facilitates placement of the device (e.g., the distal tip of the conduit) into the opening of the target ostia.

Aspects of the device may include a distal anchor configured to maintain the device within the stenotic opening during use of the device. The distal anchor may be connected to the device proximate to the distal end of the device. For example, the distal anchor may be connected to the device proximate to the distal end of the conduit. In some cases, the distal anchor is configured to prevent the device from premature explantation from the stenotic opening. The distal anchor may facilitate maintaining the device within the stenotic opening for a desired period of time until the device is removed from the stenotic opening by the user or a health care professional. In certain embodiments, the distal anchor is a mechanical anchor, such as, but not limited to, a hook, a barb, a clamp, a tether and the like. In certain cases, the distal anchor is configured to maintain the device within the stenotic opening by having a diameter that is greater than the diameter of the stenotic opening.

In some instances, the device has a frictional surface on an exterior surface of the device. The frictional surface may be configured to increase the friction between the exterior surface of the device and the surrounding tissues when the device is in use. Increasing the friction between the exterior surface of the device and the surrounding tissues may facilitate retention of the device in the stenotic opening of the subject during use. For example, the frictional surface may have a rough topography that includes an exterior surface shaped as, for example, washboard, rings, waffle pattern, snow tire pattern, pebble finish, shark skin texture, combinations thereof, and the like.

In certain cases, the device includes an adhesive disposed on an exterior surface of the device. In some cases, the membrane includes an adhesive. The membrane may be configured such that the adhesive elutes to the external surface of the device during use. The adhesive may facilitate retention of the device in the stenotic opening of the patient during use. Examples of suitable adhesives include, but are not limited to, carbomer, low molecular weight hydroxypropyl methylcellulose, polyvinyl pyrrolidone, combinations thereof, and the like.

In some cases, the distal anchor is configured to allow the device to be inserted into the stenotic opening. The distal anchor may have an outside diameter that is substantially the same as the outside diameter of the device when the device is in a non-expanded configuration. In some instances, the distal anchor has an outside diameter that is greater than the diameter of the conduit. In certain embodiments, the distal anchor has a tapered shape, such that the distal end of the distal anchor has a diameter that is less than the diameter of the proximal end of the distal anchor. In certain embodiments, the distal anchor is configured such that the distal anchor has a diameter that is smaller during insertion of the device into the stenotic opening as compared to the diameter of the distal anchor after the anchor portion of the device has been inserted into the paranasal sinus.

In certain embodiments, the distal anchor is a flexible anchor. In some cases, the flexible distal anchor is configured to have a configuration that has a smaller diameter during insertion of the device into the stenotic opening as compared to the diameter of the flexible distal anchor after the anchor portion of the device has been inserted into the paranasal sinus. For instance, the flexible distal anchor may be configured to fold into a configuration that has a smaller diameter during insertion of the device into the stenotic opening as compared to the diameter of the flexible distal anchor after the anchor portion of the device has been inserted into the paranasal sinus. The distal anchor may include one or more subunits that are connected to and extend radially outward from the conduit. The subunits of the distal anchor may be flexible, such that during insertion of the device into the stenotic opening, the subunits fold into a configuration where the distal anchor has an outside diameter that is less than the diameter of the distal anchor when the subunits are fully extended. Once the distal end of the device has been inserted into the paranasal sinus, the subunits may be free to unfold back to their extended configuration, thus anchoring the device within the stenotic opening.

Aspects of the device may include a proximal anchor configured to maintain the device within the stenotic opening during use of the device. The proximal anchor may be connected to the device proximate to the proximal end of the device. For example, the proximal anchor may be connected to the device proximate to the proximal end of the conduit. In some cases, the proximal anchor is configured to prevent the device from being inserted too far or completely into the paranasal sinus of the subject. The proximal anchor may facilitate maintaining the device within the stenotic opening for a desired period of time until the device is removed from the stenotic opening by the user or a health care professional. In some cases, the proximal anchor has an outside diameter that is greater than the diameter of the conduit. For instance, the proximal anchor may have an outside diameter that is greater than the diameter of the device when the device is in a non-expanded configuration.

In some embodiments, the device includes an attachment portion configured to facilitate removal of the device from the stenotic opening. The attachment portion may be configured to allow a removal device to be attached to the device. For example, the attachment portion of the device may include a structure, such as, but not limited to, a loop, a tether or a hook. The removal device may include a corresponding structure that allows for attachment of the removal device to the attachment portion of the device. In some instances, the device includes a loop and the removal device includes a hook. In other embodiments, the device includes a hook and the removal device includes a loop. In either embodiment, insertion of the hook into the loop connects the device to the removal device and may facilitate removal of the device from the stenotic opening.

In some cases, the attachment portion may protrude from the device to facilitate connection of the removal device to the attachment portion of the device. The attachment portion may be disposed at or near the proximal end of the device to facilitate removal of the device from the stenotic opening. For example, the attachment portion may be disposed on the proximal anchor at the proximal end of the device. In certain cases, the attachment portion may be connected to the conduit proximate to the proximal end of the device.

Additional aspects of the devices and methods for dilating a stenotic opening of a paranasal sinus in a subject are also described in U.S. patent application Ser. Nos. 13/219,505 and 13/219,497, both filed Aug. 26, 2011, and U.S. patent application Ser. No. 13/777,748, filed Feb. 26, 2013, the disclosures of each of which are incorporated herein by reference.

Kits

Also provided are kits for use in practicing the subject methods, where the kits may include one or more of the above insertion devices, and/or sinus dilators, as described above. As such, a kit may include an insertion device, and may further include one or more sinus dilators. In some instances, a sinus dilator may come preloaded on the insertion device. In some instances, the sinus dilator may come decoupled from the insertion device.

In some instances, the kit may further include additional components, such as fluid sources (e.g., water sources, saline solution sources, drug solution sources, etc.), connective tubing, guide wire, monitor, etc., which may find use in practicing the subject methods. The drugs may be provided in a separate container, such as a syringe, vial, bottle, etc., such that the drug may be filled into a drug reservoir of the insertion device prior to insertion into the stenotic opening. The drugs sources may be adapted to couple with the insertion device, such as a cartridge that is coupled to a receiving slot in the insertion device, or such as a container that is coupled to a port on the insertion device via tubing.

Furthermore, where the retention interface of the insertion device is removably coupled to the interior elongated member, the kit may further include one or more additional or different retention interfaces. Such may be desirable where the kit includes sinus dilators of different sizes and/or types, or for convenience for sanitation purposes. Various components may be packaged as desired, e.g., together or separately.

In certain embodiments, the kits include one or more sinus ostium sizing probes. In some instances, the probes are configured to be removably mountable onto the distal end of the insertion device (e.g., on the distal end of the hollow elongated member of the device). In certain cases, the probes are of varying diameters and adapted to be inserted into the dilated ostium to determine the diameter of the dilated ostium and assess whether further dilation is needed. In certain embodiments, such probes can be made from light-transmitting materials in order to illuminate the probes during dilated ostium measurement.

In addition to above mentioned components, the subject kits may further include instructions for using the components of the kit to practice the subject methods. The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, DVD, Blu-Ray, computer-readable memory, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

As can be appreciated from the disclosure provided above, the present disclosure has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Figure 11A:
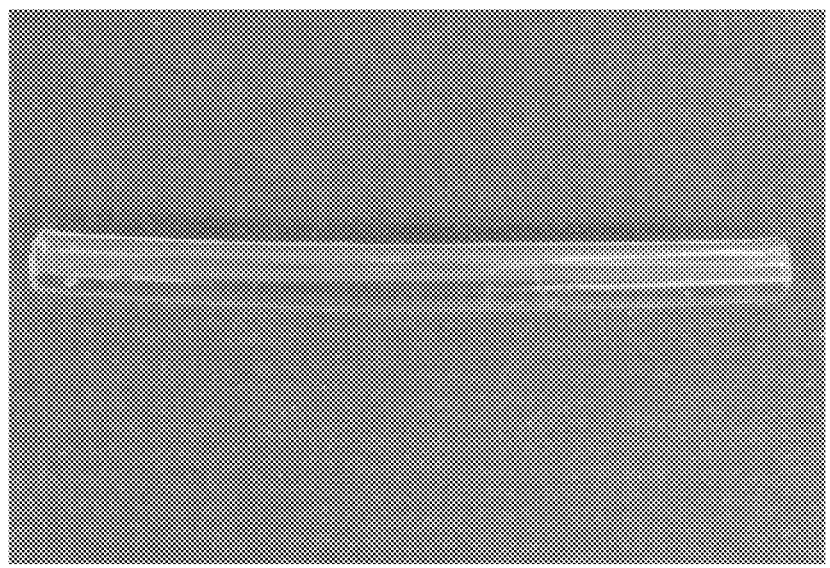
FIGS. 11A and 11B show a tube that includes an inner tube where a portion of the outer surface of the inner tube has a hydrophilic material disposed thereon, according to embodiments of the present disclosure.
Figure 11B:
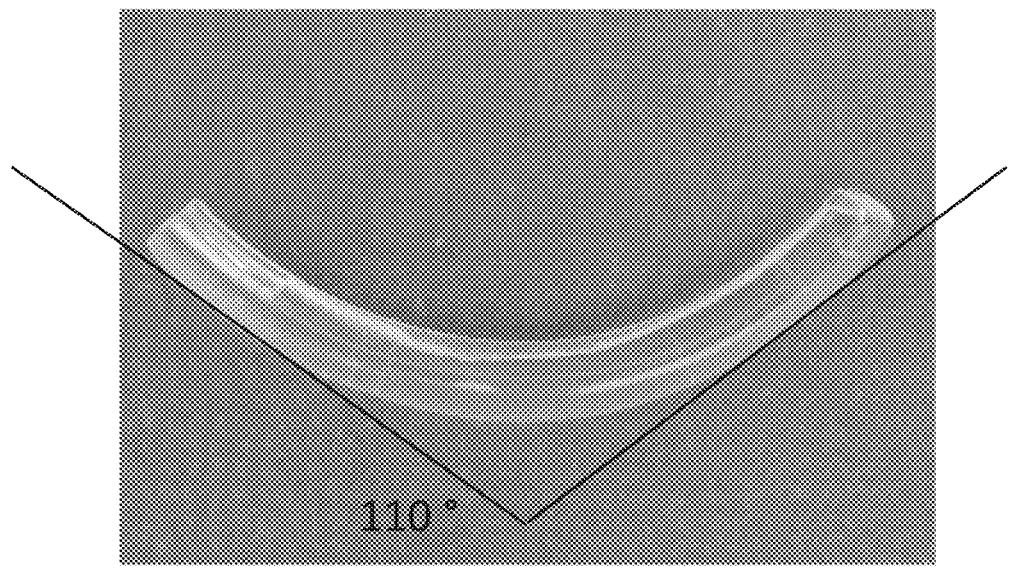

Experiments were performed using an embodiment where a portion of a tube as described herein was coated with a water swellable (e.g., hydrophilic) material. The tube included an inner tube composed of 30 mm Carbothane grade PC-3572D (hydrophobic polymer) with a 74 mil (1.9 mm) outside diameter and 50 mil (1.3 mm) inside diameter. The longitudinal outer half of the inner tube was laminated with 30 mm Tecophilic HP-93A-100 (hydrophilic polymer) with a 104 mil (2.6 mm) outer diameter and 38 mil (1 mm) inner diameter. FIG. 11A shows an image of the tube before hydration. The tube was hydrated at room temperature in de-ionized water for 2 hours. As shown in FIG. 11B, after hydration for 2 hours, the hydrophilic polymer underwent localized swelling which placed the tube into a curved configuration with a bend angle of 110°.

The preceding merely illustrates the principles of the disclosure. All statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present disclosure, therefore, is not intended to be limited to the exemplary embodiments shown and described herein. Rather, the scope and spirit of present disclosure is embodied by the appended claims.

What is claimed is:

1. A device for inserting a sinus dilator into a stenotic opening of a paranasal sinus of a subject, the insertion device comprising:
 a handheld member comprising a handle and an actuator;
  a hollow elongated member having a proximal end coupled to the handheld member and a distal end having an opening to an interior cavity of the hollow elongated member;
 an interior elongated member operatively connected to the actuator and extending within the interior cavity of the hollow elongated member;
  a tube engaged to the distal end of the hollow elongated member, wherein the tube comprises a material configured to transition from a first configuration to a second configuration, the first configuration such that the tube is aligned with a longitudinal axis of the hollow elongated member and the second configuration such that the tube is bent relative to the longitudinal axis of the hollow elongated member; and
  a sinus dilator operatively coupled to the insertion device, wherein the sinus dilator is positioned within one or more of the hollow elongated member or the tube.

2. The insertion device of claim 1, wherein the material comprises a shape-memory material.

3. The insertion device of claim 2, wherein the shape-memory material comprises a shape-memory alloy.

4. The insertion device of claim 3, wherein the shape-memory alloy comprises nickel and titanium.

5. The insertion device of claim 2, wherein the shape-memory material comprises a shape-memory polymer.

6. The insertion device of claim 5, wherein the shape-memory polymer comprises polyurethane, polyethylene terephthalate (PET), polyethyleneoxide (PEO), polystyrene, polybutadiene, polyoxazoline, polytetrahydrofuran, polynorbornene, polyether ether ketone (PEEK), or combinations thereof.

7. The insertion device of claim 1, wherein a portion of the tube comprises a hydrophilic material.

8. The insertion device of claim 7, wherein the tube comprises an inner tube with the hydrophilic material disposed on a portion of an outer surface of the inner tube.

9. The insertion device of claim 1, wherein the second configuration is such that the tube has a bend angle of 60° to 120° relative to the longitudinal axis of the hollow elongated member.

10. The insertion device of claim 9, wherein the bend angle is 110°.

11. The insertion device of claim 9, wherein the bend angle is 70°.

12. The insertion device of claim 1, wherein the interior elongated member is relatively displaceable with respect to the hollow elongated member such that upon actuation of the actuator, the interior elongated member is displaced within the hollow elongated member.

13. The insertion device of claim 1, wherein the tube is slidably engaged to an exterior surface of the hollow elongated member.

14. The insertion device of claim 1, wherein the tube is slidably engaged to an interior surface of the hollow elongated member.

15. The insertion device of claim 1, wherein the sinus dilator is removably coupled to the insertion device.

16. The insertion device of claim 1, wherein the sinus dilator is coupled to a distal end of the tube.

17. The insertion device of claim 1, wherein the sinus dilator is positioned within the hollow elongated member.

18. The insertion device of claim 1, wherein the tube is radially expandable.

19. A method of inserting a sinus dilator in a stenotic opening of a paranasal sinus in a subject, the method comprising:
 placing the distal end of the hollow elongated member of the insertion device according to claim 1 into a nasal cavity of the subject;
 inserting the sinus dilator in the stenotic opening; and
 removing the insertion device from the nasal cavity of the subject.

20. The method of claim 19, comprising extending the tube from the distal end of the hollow elongated member.

21. The method of claim 19, wherein inserting the sinus dilator comprises relatively displacing the interior elongated member with respect to the hollow elongated member and the tube while the hollow elongated member remains in a relatively fixed position to the handheld member.

22. The method of claim 19, wherein the stenotic opening is a stenotic opening of a maxillary sinus of the subject.

23. The method of claim 19, wherein the inserting occurs while the tube is in the second configuration.

24. The method of claim 23, wherein the sinus dilator is coupled to a distal end of the tube, and inserting the sinus dilator comprises distally displacing the interior elongated member within the hollow elongated member and the tube.

25. The method of claim 23, wherein the sinus dilator is positioned within the hollow elongated member and operatively coupled to a distal end of the interior elongated member, and inserting the sinus dilator comprises distally displacing the interior elongated member and the sinus dilator through the hollow elongated member and the tube.

26. A kit comprising:
 an insertion device and a sinus dilator according to claim 1; and
 a packaging.

* * * * *